(12) United States Patent
Hossainy et al.

(10) Patent No.: US 6,908,624 B2
(45) Date of Patent: Jun. 21, 2005

(54) COATING FOR IMPLANTABLE DEVICES AND A METHOD OF FORMING THE SAME

(75) Inventors: Syed F. A. Hossainy, Fremont, CA (US); Steven Z. Wu, Hillsborough, NJ (US); Manish Gada, Santa Clara, CA (US); Anthony Andreacchi, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 60 days.

(21) Appl. No.: 10/320,935

(22) Filed: Dec. 16, 2002

(65) Prior Publication Data

US 2004/0086542 A1 May 6, 2004

Related U.S. Application Data

(63) Continuation-in-part of application No. 09/750,595, filed on Dec. 28, 2000, which is a continuation-in-part of application No. 09/470,559, filed on Dec. 23, 1999.

(51) Int. Cl.$^7$ ................................................ A61F 2/00
(52) U.S. Cl. .................... 424/424; 424/400; 424/422; 514/822; 623/1.15; 623/1.42; 623/1.43; 623/1.44; 623/1.46; 623/1.49
(58) Field of Search .............................. 424/400, 422, 424/424; 623/1.15, 1.42, 1.43, 1.44, 1.46, 1.49, 1.2; 514/822

(56) References Cited

U.S. PATENT DOCUMENTS

| | | | |
|---|---|---|---|
| 4,329,383 A | 5/1982 | Joh | 428/36 |
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 4,941,870 A | 7/1990 | Okada et al. | 600/36 |
| 4,977,901 A | 12/1990 | Ofstead | 128/772 |
| 5,112,457 A | 5/1992 | Marchant | 204/165 |
| 5,165,919 A | 11/1992 | Sasaki et al. | 424/488 |

(Continued)

FOREIGN PATENT DOCUMENTS

| | | |
|---|---|---|
| EP | 0 310 856 | 4/1989 |
| EP | 0 665 023 | 8/1995 |
| EP | 0 879 595 | 11/1998 |
| EP | 0 970 711 | 1/2000 |
| WO | WO 91/12846 | 9/1991 |
| WO | WO 96/40174 | 12/1996 |
| WO | WO 97/45105 | 12/1997 |
| WO | WO 98/17331 | 4/1998 |
| WO | WO 99/01118 | 1/1999 |
| WO | WO 99/63981 | 12/1999 |
| WO | WO 00/02599 | 1/2000 |
| WO | WO 00/12147 | 3/2000 |
| WO | WO 00/64506 | 11/2000 |
| WO | WO 01/01890 A1 | 1/2001 |
| WO | WO 01/45763 | 6/2001 |
| WO | WO 02/056790 | 7/2002 |
| WO | WO 02/058753 | 8/2002 |
| WO | WO 02/074194 | 9/2002 |
| WO | WO 03/035131 | 5/2003 |
| WO | WO 03/090818 | 11/2003 |

OTHER PUBLICATIONS

Anonymous, *Rolling Therapeutic Agent Loading Device for Therapeutic Agent Delivery or Coated Stent* (Abstract 434009), Res. Disclos. pp. 975–976(Jun. 2000).

(Continued)

*Primary Examiner*—Gary Kunz
*Assistant Examiner*—Konata M. George
(74) *Attorney, Agent, or Firm*—Squire, Sanders & Dempsey

(57) ABSTRACT

Coatings for implantable devices or endoluminal prosthesis, such as stents, are provided, including a method of forming the coatings. The coatings can be used for the delivery of an active ingredient or a combination of active ingredients.

32 Claims, 8 Drawing Sheets

U.S. PATENT DOCUMENTS

| | | | |
|---|---|---|---|
| 5,272,012 A | 12/1993 | Opolski | 428/423.1 |
| 5,328,471 A | 7/1994 | Slepian | 604/101 |
| 5,380,299 A | 1/1995 | Fearnot et al. | 604/265 |
| 5,417,981 A | 5/1995 | Endo et al. | 424/486 |
| 5,455,040 A | 10/1995 | Marchant | 424/426 |
| 5,464,650 A | 11/1995 | Berg et al. | 427/2.3 |
| 5,578,073 A | 11/1996 | Haimovich et al. | 623/1 |
| 5,605,696 A | 2/1997 | Eury et al. | 424/423 |
| 5,609,629 A | 3/1997 | Fearnot et al. | 623/1 |
| 5,628,730 A | 5/1997 | Shapland et al. | 604/21 |
| 5,667,767 A | 9/1997 | Greff et al. | 424/9.411 |
| 5,670,558 A | 9/1997 | Onishi et al. | 523/112 |
| 5,700,286 A | 12/1997 | Tartaglia et al. | 623/1 |
| 5,702,754 A | 12/1997 | Zhong | 427/2.12 |
| 5,716,981 A | 2/1998 | Hunter et al. | 514/449 |
| 5,776,184 A | 7/1998 | Tuch | 623/1 |
| 5,800,392 A | 9/1998 | Racchini | 604/96 |
| 5,824,049 A | 10/1998 | Ragheb et al. | 623/1 |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,877,224 A | 3/1999 | Brocchini et al. | 514/772.2 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,015,541 A | 1/2000 | Greff et al. | 424/1.25 |
| 6,033,582 A | 3/2000 | Lee et al. | 216/37 |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,245,753 B1 | 6/2001 | Byun et al. | 514/56 |
| 6,258,121 B1 | 7/2001 | Yang et al. | 623/1.46 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,331,313 B1 | 12/2001 | Wong et al. | 424/427 |
| 6,335,029 B1 * | 1/2002 | Kamath et al. | 424/423 |
| 6,379,381 B1 | 4/2002 | Hossainy et al. | 623/1.42 |
| 6,451,373 B1 | 9/2002 | Hossainy et al. | 427/2.25 |
| 6,503,954 B1 | 1/2003 | Bhat et al. | 514/772.2 |
| 2001/0037145 A1 | 11/2001 | Guruwaiya et al. | 623/1.15 |
| 2002/0123801 A1 | 9/2002 | Pacetti et al. | 623/1.46 |

OTHER PUBLICATIONS

Dichek et al., *Seeding of Intravascular Stents with Genetically Engineered Endothelial Cells*, Circ. 80(5):1347–1353 (Nov. 1989).

Herdeg et al., *Antiproliferative Stent Coatings: Taxol and Related Compounds*, Semin. Intervent. Cardiol. 3:197–199 (1998).

Miyazawa et al., *Effects of pemirolast and Tranilast on Intimal Thickening After Arterial Injury in the Rat*, J. Cardiovasc. Pharmacol., pp. 157–162 (1997).

Ohsawa et al., *Preventive Effects of an Antiallergic Drug, Pemirolast Potassium, on Restenosis After Percutaneous Transluminal Coronary Angioplasty*, American Heart Journal, pp. 1081–1087 (Dec. 1998).

Shigeno, *Prevention of Cerebrovascular Spasm By Bosentan, Novel Endothelin Receptor*, Chemical Abstract 125:212307 (1996).

Barath et al., *Low Dose of Antitumor Agent Prevents Smooth Muscle Cell Proliferation After Endothelial Injury*; JACC 13(2):252A (Abstract) (Feb. 1989).

Matsumaru et al., *Embolic Materials For Endovascular Treatment of Cerebral Lesions*; J. Biomater. Sci. Polymer Edn, 8(7):555–569 (1997).

Miyazaki et al., "*Antitumor Effect of Implanted Ethylene–Vinyl Alcohol Copolymer Matrices Containing Anticancer Agents on Ehrlich Ascites Carcinoma and P388 Leukemia in Mice*," Chem. Pharm. Bull., 33(6):2490–2498 (1985).

\* cited by examiner

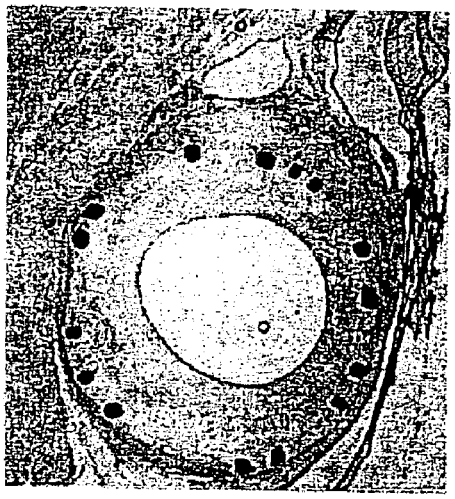
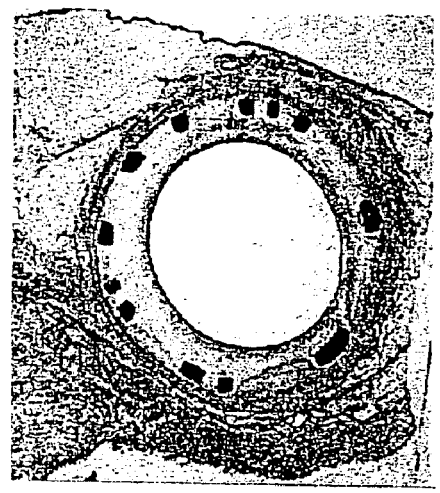
FIG. 6A                FIG. 6B
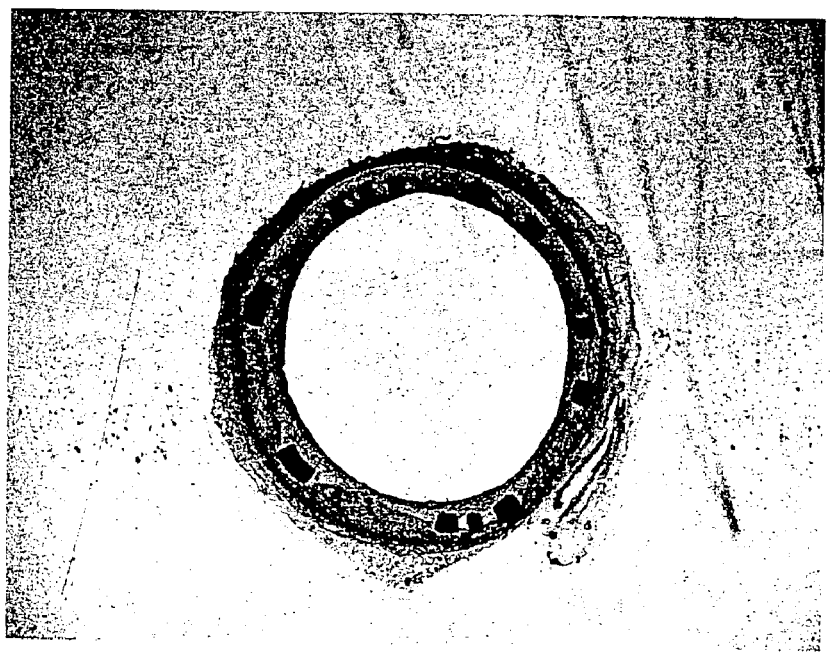
FIG. 7A

COATING FOR IMPLANTABLE DEVICES AND A METHOD OF FORMING THE SAME

CROSS-REFERENCE

This is a continuation-in-part of U.S. patent application Ser. No. 09/750,595 filed on Dec. 28, 2000, which is a continuation-in-part of U.S. patent application Ser. No. 09/470,559 filed on Dec. 23, 1999.

BACKGROUND

1. Field of the Invention

The invention relates to coatings and methods of forming the coatings on implantable devices or endoluminal prostheses, such as stents.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion for remodeling of the vessel wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Vasospasms and recoil of the vessel wall also threaten vessel closure. Moreover, thrombosis and restenosis of the artery may develop over several months after the procedure, which may require another angioplasty procedure or a surgical by-pass operation. To reduce the partial or total occlusion of the artery by the collapse of arterial lining, and to reduce the chance of the development of thrombosis and restenosis, an expandable, intraluminal prosthesis, one example of which includes a stent, is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Mechanical intervention via stents has reduced the rate of restenosis as compared to balloon angioplasty; but restenosis is still a significant clinical problem with rates ranging from 20–40%. When restenosis does occur in the stented segment, its treatment can be challenging, as clinical options are more limited as compared to lesions that were treated solely with a balloon.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. The embodiments of the present invention provide stent coatings for local delivery of drugs.

SUMMARY

In accordance with one aspect of the present invention, a method of forming a coating for an implantable device is provided. The method includes forming a primer layer comprising a polymer on at least a portion of a surface of an implantable device, wherein the primer layer has a weight measurement of X, and forming a reservoir layer comprising a polymer and an active ingredient on at least a selected portion of the primer layer, wherein the reservoir layer has a weight measurement of Y and wherein X/Y is equal to or greater than 0.25. In one embodiment, the coating has a drug loading equal to or greater than 30%. In another embodiment, the method further comprises forming asperities on the surface of the primer layer preceding the formation of the reservoir layer. In yet another embodiment, the primer layer includes at least a region having a degree of porosity.

In another aspect, a method of forming a coating for an implantable device is provided. The method includes forming a primer layer comprising a polymer on at least a portion of a surface of an implantable device, wherein the primer layer has a thickness X and forming a reservoir layer comprising a polymer and an active ingredient on at least a selected portion of the primer layer, wherein the reservoir layer has a thickness Y and wherein X/Y is equal to or greater than 0.25. In one embodiment, the thickness X is about 0.5 microns to about 3 microns and the thickness Y is about 1 micron to about 10 microns.

In yet another aspect of the present invention, an implantable device is provided comprising a coating for delivery of an active ingredient. The coating includes a primer region comprising a polymer on at least a portion of a surface of an implantable device, wherein the primer region has a thickness X, and a reservoir region comprising a polymer and an active ingredient on at least a selected portion of the primer region, wherein the reservoir region has a thickness Y, and wherein X/Y is equal to or greater than 0.25. The thickness X is measured from the outer surface of the primer region to the surface of the implantable device prior to the migration of the active ingredient from the reservoir region to the primer region. In one embodiment, the coating further includes a barrier region located on at least a selected portion of the reservoir region for reducing the rate at which the active ingredient is released from the coating after insertion of the device into a body of a patient. In another embodiment, the primer region includes a porous matrix extending from the interface of the primer region and the reservoir region into the primer.

In another aspect, a stent comprising a coating for delivery of an active ingredient is provided, wherein the coating includes a primer region comprising a polymer and a reservoir region comprising a polymer and an active ingredient, and wherein the thickness or the weight of the primer region is sufficiently high so as to allow drug loading of 30% in the reservoir region without causing the coating to significantly crack when the stent is expanded.

BRIEF DESCRIPTION OF THE FIGURES

FIG. 6A is a picture of a histology slide of a coronary vessel from the control group in accordance with Example 16;

FIG. 6B is a picture of a histology slide of a coronary vessel from the actinomycin D group in accordance with Example 16;

FIG. 7A is a picture of a histology slide of a coronary vessel from the control group in accordance with Example 26;

DETAILED DESCRIPTION OF THE EMBODIMENTS

For ease of discussion, the methods and apparatus detailed herein will be described with reference to a coating for a stent. However, the implantable device coated in accordance with embodiments of the present invention may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), stainless steel (316L), "MP35N," "MP20N," elastinite (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Coating

Figure 1A:
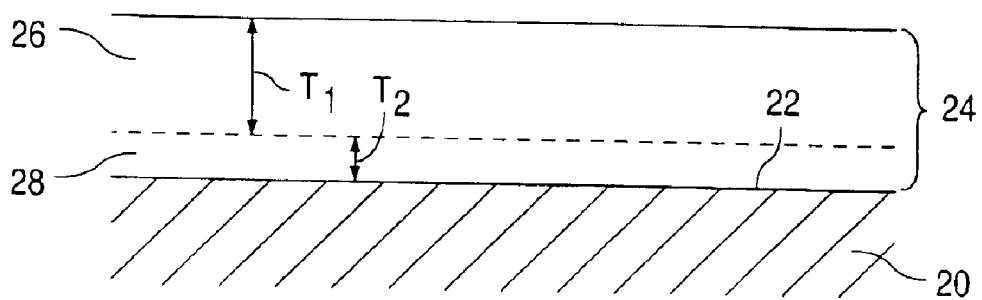
FIGS. 1A–1E illustrate coatings in accordance with some of the embodiments of the present invention.
Figure 1B:
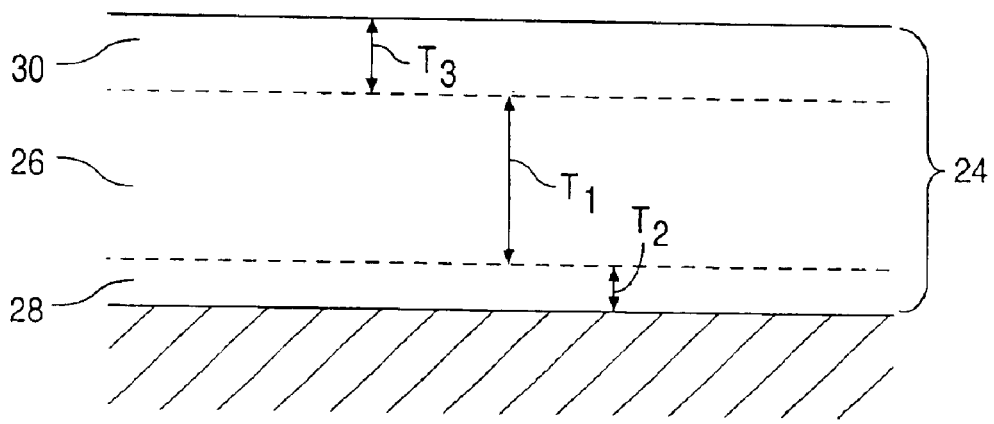

Referring to FIG. 1A, a body of a stent 20 is illustrated having a surface 22, e.g., a metallic surface such as stainless steel. A coating 24 is disposed on surface 22. Coating 24 includes a reservoir region 26 containing an active ingredient. A primer region 28 that is substantially free of any active ingredients is disposed underneath at least a portion of reservoir region 26. As illustrated in FIG. 1B, coating 24 can also include a barrier region 30 that is substantially free of any active ingredients. The Figures have not been drawn to scale, and the depth and thickness of the various regions and layers have been over or under emphasized for illustrative purposes.

In one embodiment of the present the invention, the interface between the primer region and the reservoir region is modified to increase the permeability of the primer layer to the active ingredient. The interface can be modified using one of several methods. These methods include, for example, partially blending of the polymers of the primer region with the polymers of the reservoir region, modifying the surface of the primer layer by forming areas of roughness, or forming a porous matrix on the surface of the primer layer, as more fully described below.

The interface between the primer region and the reservoir region can be modified by partially blending the polymers of the primer region with the polymers of the reservoir region during the coating process through the use of a common solvent. For example, primer region 28 can be formed on stent 20 by applying a primer coating composition having a polymer dissolved in a solvent. Stent 20 can then be baked to essentially remove the solvent in the composition to form the coating. Subsequently, another composition is applied having a polymer, a solvent and an active ingredient dispersed therein. If the solvent in the active ingredient composition is capable of dissolving the polymer in the primer layer, then the polymers of the primer region and the reservoir region will intermix or blend. This blending can allow the active ingredient to be absorbed or flux into primer layer 28.

In another embodiment, asperities, or areas of roughness, are formed on the surface of the primer layer to increase the permeability of the primer layer. The asperities enable the primer region to physically entrap the reservoir region. In addition, the asperities can promote the migration of the active ingredient from the reservoir region to the primer region through capillary action. Because the active ingredient migrates into the deeper portions of the coating, the diffusion rate of the active ingredient from the coating is decreased when the coated device is inserted into a body of a patient. As a result, the asperities can promote an increased residence time of the active ingredient and thereby prevent the "burst effect" of the active ingredient from the coating. "Burst effect" refers to the quick release of an active ingredient from a polymeric coating when the device is inserted into a biological lumen.

The primer region can include a porous matrix extending from the interface of the primer region and the reservoir region into the primer region. The porous matrix can extend partially into the primer region, or all the way up to the surface of the implantable device. The active ingredient can migrate from the reservoir region by capillary action into the primer region.

In another embodiment of the present invention, the thickness of the primer region is increased relative to the thickness of the reservoir region. The thicker primer region can decrease the diffusion rate of the active ingredient from the coating. Additionally, by increasing the thickness of the primer region, the primer region can act as a more effective tie layer between the surface of the device and the reservoir region. For example, the thicker primer region can reduce or prevent the formation of cracks in the stent coating as the stent is expanded as shown in Examples 37–39. Typically the presence of an active ingredient in a polymeric matrix interferes with the ability of the matrix to adhere effectively to the surface of the device. An increase in the quantity of the active ingredient reduces the effectiveness of the adhesion. High drug loadings of, for example, 10–40% by weight in the coating significantly hinder the retention of the coating on the surface of the device. "Drug loading" means the percentage ratio of active ingredient to polymer by weight. By increasing the thickness of primer region 28 relative to reservoir region 26, primer region 28 can allow for the quantity of the active ingredient in reservoir region 26 to be increased without compromising the ability of reservoir region 26 to be effectively contained on the device during delivery and, if applicable, expansion of the device. For instance, as demonstrated in Example 37, the coating of the present invention has superior results when the drug loading is relatively high. In particular, the mechanical integrity of the coating of the present invention can withstand expansion of the stent (i.e., the coating does not significantly peel or crack) even when the drug loading in the coating is relatively high. In one embodiment of the present invention, drug loadings equal to or greater than 30% can be achieved.

Referring to FIG. 1B, by way of example, reservoir region 26 for coating 24 can have a thickness $T_1$, of about 0.5 microns to about 10 microns. Primer region 28 can have a thickness $T_2$, examples of which can be in the range of about 0.1 to about 10 microns, more narrowly about 0.5 to about 5 microns. The thickness of the reservoir region $T_1$, is measured from the outer surface of the reservoir region to the primer region prior to the migration of the active ingredient from the reservoir region to the primer region. Similarly, the thickness of the primer region $T_2$ is measured from the outer surface of the primer region to the surface of the stent prior to the migration of the active ingredient from the reservoir region to the primer region. In an embodiment of the present invention, $T_2/T_1$ is greater than or equal to 0.25. In another embodiment, $T_2/T_1$ is greater than or equal to 0.33. The particular thicknesses $T_1$, and $T_2$ are based in part on the type of procedure for which stent 20 is employed and the amount of the active ingredient that is desired to be delivered.

Figure 1C:
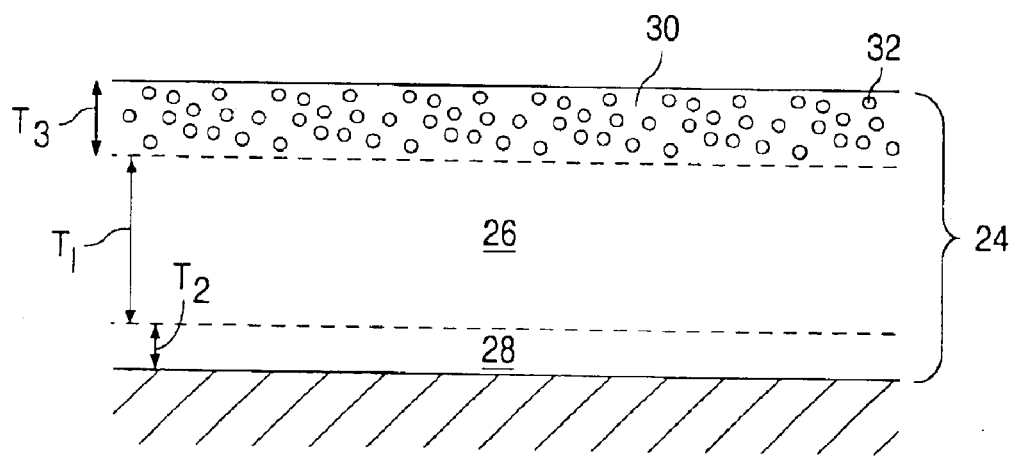

Referring to FIG. 1B, diffusion barrier region 30 can have any suitable thickness $T_3$, as the thickness $T_3$ is dependent on parameters such as, but not limited to, the desired rate or duration of release and the procedure for which stent will be used. Diffusion barrier region 30 can have a thickness $T_3$ of about 0.1 to about 10 microns, more narrowly from about 0.25 to about 2 microns. Additionally, referring to FIG. 1C, barrier layer 30 can contain particles 32 to reduce the rate of release of the active ingredient from the coating. If particles are employed, for a smooth outer surface, the size of particles should not be greater than about 10% of thickness $T_3$ of diffusion barrier region 30. Additionally, the particle volume fraction $X_p$ should not exceed about 0.74. Packing density or particle volume fraction $X_p$ can be defined by the following equation:

$$X_p = V_{particles}/(V_{particles} + V_{polymer})$$

wherein V is volume.

Figure 1D:
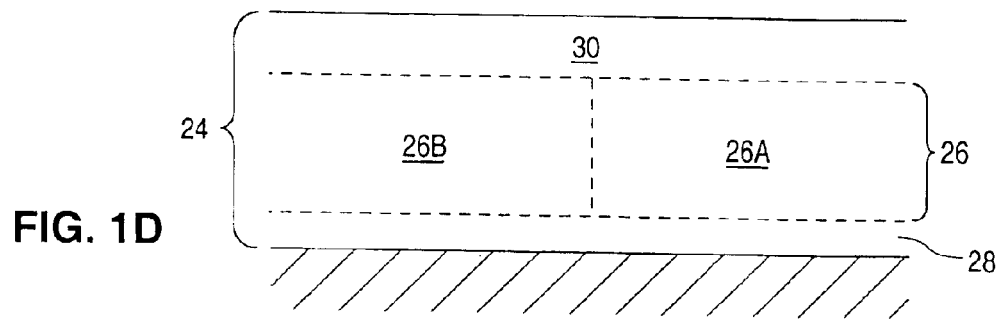

Each of the layers of the polymeric coating can have different sections with different properties in order to provide a coating with variable active ingredient release parameters. As illustrated in FIG. 1D, for example, reservoir region 26 can include first and second reservoir sections 26A and 26B, each containing a different active ingredient, e.g., actinomycin D and taxol, respectively. Accordingly, coating 24 can carry a combination of at least two different active ingredients for sustained delivery. First and second sections 26A and 26B can be deposited by, for example, masking the area of primer region 28 over second section 26B and applying a first composition containing a first active ingredient to form first section 26A. First section 26A can then be masked and a second composition containing a second active ingredient can be applied to form second section 26B. This procedure can be followed to form any suitable number of sections containing a different active ingredient.

Figure 1E:
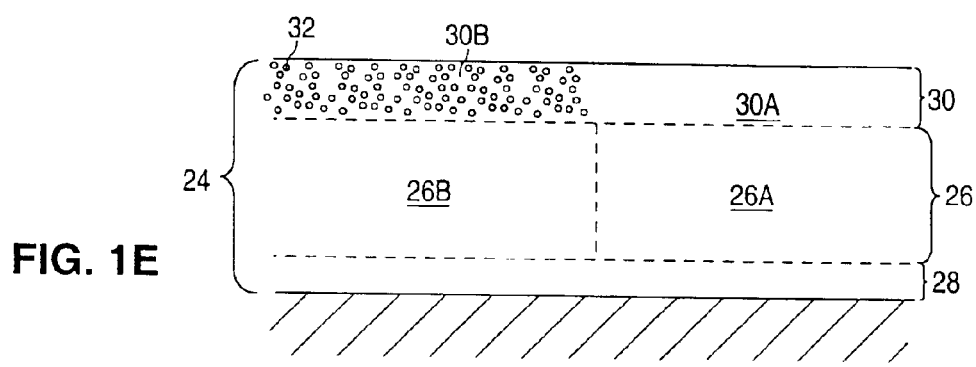

Barrier region 30 can be formed on reservoir sections 26A and 26B, as illustrated in FIG. 1D. Referring to FIG. 1E, barrier region 30 can also include a first barrier section 30A disposed over first reservoir section 26A containing a first active ingredient, e.g., actinomycin D. A second barrier section 30B can be formed over second reservoir section 26B containing a second active ingredient, e.g., taxol. First barrier section 30A is particle free and second barrier section 30B contains particles 32. As a result, coating 24 harbors two different release parameters for each of the active ingredients contained in reservoir sections 26A and 26B.

Figure 2A:
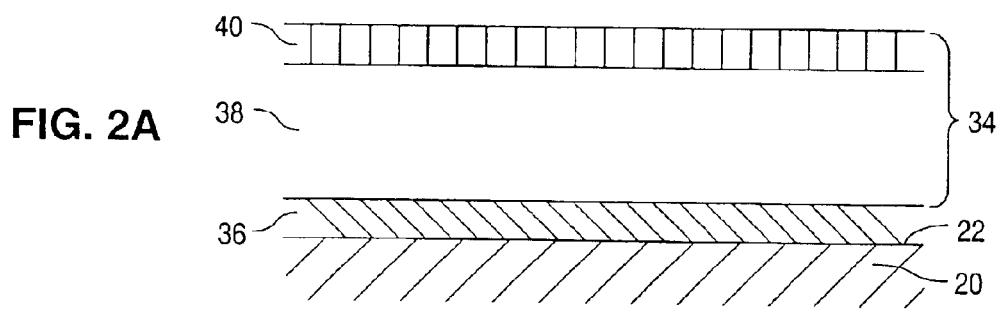
FIGS. 2A and 2B illustrate coatings having different layers.

Different polymeric materials having interfacial compatibilities can be used to form individual, distinct layers for the primer, reservoir, and diffusion barrier components of the coating. Referring to FIG. 2A, a coating 34 is provided having a primer region 36, made from a first polymeric material, formed on surface 22 of stent 20. A reservoir region 38 made from a second polymeric material is deposited on a selected area of primer region 36. A barrier region 40, made from a third polymeric material can be deposited on reservoir region 38. Examples of different polymeric materials having interfacial compatibilities include, for example, an EVAL primer with a reservoir layer of ethylene vinylacetate; a poly(n-butyl methacrylate) primer with an EVAL reservoir layer; an EVAL primer and a reservoir layer of polycaprolactone; and an epoxy primer consisting of the diglycidylether of bisphenol A cured with polyamine curatives with an EVAL reservoir layer. Other combinations can be derived by one of ordinary skill in the art.

Figure 2B:
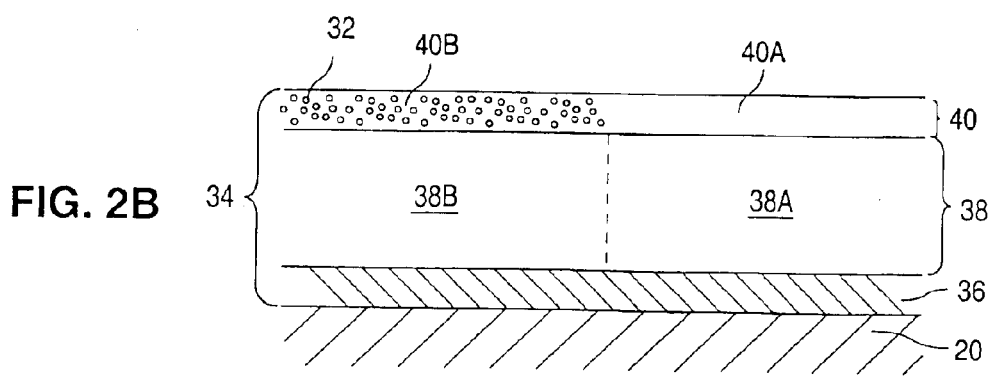

One of ordinary skill in the art can appreciate that a variety of coating combinations can be provided. For example, as illustrated in FIG. 2B, coating 34 contains primer region 36 made from a first polymeric material. Reservoir region 38, made from a second polymeric material, is formed on primer region 36. Reservoir region 38 contains first and second sections, illustrated as 38A and 38B. First and second sections 38A and 38B each contain a different active ingredient. Barrier region 40, made from a third polymeric material, can be deposited on reservoir region 38. Barrier region 40 includes a first section 40A deposited over first section 38A of reservoir region 38. Barrier region 40 additionally includes a second section 40B deposited over second section 38B of reservoir region 38. Second section 40B can include particles 32 and/or be made out of a fourth polymeric material to create a variety of different release parameters.

Composition for the Primer Layer

The embodiments of the composition for a primer layer are prepared by conventional methods wherein all components are combined, then blended. More particularly, a predetermined amount of a polymer or a prepolymer is added to a predetermined amount of a solvent or a combination of solvents. The mixture can be prepared in ambient pressure and under anhydrous atmosphere. If necessary, a free radical or UV initiator can be added to the composition for initiating the curing or cross-linking of the prepolymer. Heating and stirring and/or mixing can be employed to effect dissolution of the polymer into the solvent.

"Polymer," "poly," and "polymeric" are defined as compounds that are the product of a polymerization reaction and are inclusive of homopolymers, copolymers, terpolymers etc., including random, alternating, block, and graft variations thereof. The polymers should have a high capacity of adherence to the surface of an implantable device, such as a metallic surface of a stent. Stainless steel, such as 316L, is a commonly used material for the manufacturing of a stent. Stainless steel includes a chromium oxide surface layer which makes the stent corrosion resistant and confers, in large part, biocompatibility properties to the stent. The chromium oxide layer presents oxide, anionic groups, and hydroxyl moieties, which are polar. Consequently, polymeric materials with polar substituents and cationic groups can adhere to the surface. Representative examples of suitable polymeric material include polyisocyanates, unsaturated polymers, high amine content polymers, acrylates, polymers with high content of hydrogen bonding groups, silane coupling agents, titanates and zirconates.

Representative examples of polyisocyanates include triisocyanurate, aliphatic polyisocyanate resins based on hexamethylene diisocyanate, aromatic polyisocyanate prepolymers based on diphenylmethane diisocyanate, polyisocyanate polyether polyurethanes based on diphenylmethane diisocyanate, polymeric isocyanates based on toluene diisocyanate, polymethylene polyphenyl isocyanate, and polyester polyurethanes.

Representative examples of unsaturated polymers include polyester diacrylates, polycaprolactone diacrylates, polyester diacrylates, polytetramethylene glycol diacrylate, polyacrylates with at least two acrylate groups, polyacrylated polyurethanes, and triacrylates. With the use of unsaturated prepolymers a free radical or UV initiator can be added to the composition for the thermal or UV curing or cross-linking process. For thermal curing, examples of free radicals initiators are benzoyl peroxide; bis(2,4-dichlorobenzoyl)peroxide; dicumyl peroxide; 2,5-bis(tert-butyl peroxy)-2,5-dimethyl hexane; ammonium persulfate, and 2,2'-azobisisobutyronitrile. As is understood by one of ordinary skill in the art, each initiator requires a different temperature to induce decomposition. For UV curing, examples of initiators include 2,2-dimethoxy-2-phenylacetophenone; 1-hydroxycyclohexyl phenyl ketone; benzoin ethyl ether; and benzophenone. These initiators can be activated by illumination with a medium pressure Hg bulb that contains wavelengths between 250 and 350 nm.

Representative examples of high amine content polymers include polyethyleneamine, polyallylamine, and polylysine.

Representative examples of acrylates include copolymers of ethyl acrylate, methyl acrylate, methacrylic acid, acrylic acid, and cyanoacrylates.

Representative examples of high content of hydrogen bonding group polymers include polyethylene-co-polyvinyl alcohol, epoxy polymers based on the diglycidylether of bisphenol A with amine crosslinking agents, epoxy polymers cured by polyols and lewis acid catalysts, epoxy phenolics, epoxy-polysulfides, ethylene vinyl acetate, melamine formaldehydes, polyvinylalcohol-co-vinyl acetate polymers, resorcinol-formaldehydes, urea-formaldehydes, polyvinylbutyral, polyvinylacetate, alkyd polyester resins, acrylic acid modified ethylene vinyl acetate polymers, methacrylic acid modified ethylene vinyl acetate polymers, acrylic acid modified ethylene acrylate polymers, methacrylic acid modified ethylene acrylate polymers, anhydride modified ethylene acrylate copolymers, and anhydride modified ethylene vinyl acetate polymers.

Representative examples of silane coupling agents include 3-aminopropyltriethoxysilane and (3-glydidoxypropyl)methyldiethoxysilane.

Representative examples of titanates include tetra-isopropyl titanate and tetra-n-butyl titanate.

Representative examples of zirconates include n-propyl zirconate and n-butyl zirconate.

Biocompatible polymers can also be used for the primer material. Examples of biocompatible primers include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoesters, polyanhydrides, poly(glycolic acid), poly(D,L-lactic acid), poly(glycolic acid-co-trimethylene carbonate), polyphosphoesters, polyphosphoester urethanes, poly(amino acids), cyanoacrylates, poly(trimethylene carbonates), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. Also, polyurethanes, silicones, and polyesters could be used and other polymers could also be used if they can be dissolved and cured or polymerized on the stent such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

A representative example of a very suitable choice of polymer for the primer layer is poly(butyl methacrylate) (PBMA). Ethylene vinyl alcohol is also functionally a very suitable choice of polymer. Ethylene vinyl alcohol copolymer, commonly known by the generic name EVOH or by the trade name EVAL, refers to copolymers comprising residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. In a useful embodiment, the copolymer comprises a mole percent of ethylene of from about 27% to about 47%. Typically, 44 mole percent ethylene is suitable. Ethylene vinyl alcohol copolymers are available commercially from companies such as Aldrich Chemical Company, Milwaukee, Wis., or EVOH Company of America, Lisle, Ill., or can be prepared by conventional polymerization procedures that are well known to one of ordinary skill in the art. The copolymer possesses good adhesive qualities to the surface of a stent, particularly stainless steel surfaces, and has illustrated the ability to expand with a stent without any significant detachment of the copolymer from the surface of the stent.

The solvent should be mutually compatible with the polymer and should be capable of placing the polymer into solution at the concentration desired in the solution. Useful solvents should also be able to expand the chains of the polymer for maximum interaction with the surface of the device, such as a metallic surface of a stent. Examples of solvent can include, but are not limited to, dimethylsulfoxide (DMSO), chloroform, water (buffered saline), xylene, acetone, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methyl pyrrolidinone, toluene and mixtures thereof.

By way of example, and not limitation, the polymer can comprise from about 0.1% to about 35%, more narrowly about 2% to about 20% by weight of the total weight of the composition, and the solvent can comprise from about 65% to about 99.9%, more narrowly about 80% to about 98% by weight of the total weight of the composition. A specific weight ratio is dependent on factors such as the material from which the implantable device is made and the geometrical structure of the device.

Figure 3A:
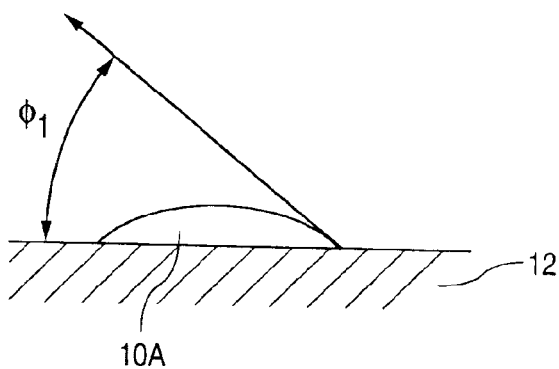
FIG. 3A illustrates a fluid on a solid substrate having a contact angle $\Phi_1$.
Figure 3B:
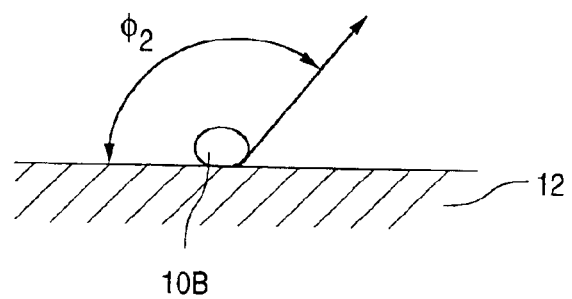
FIG. 3B illustrates a fluid on a solid substrate having a contact angle $\Phi_2$.

A fluid can also be added to the composition to enhance the wetting of the composition for a more uniform coating application. To enhance the wetting of the composition, a suitable fluid typically has a high capillary permeation. Capillary permeation or wetting is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. FIG. 3A illustrates a fluid droplet 10A on a solid substrate 12, for example a stainless steel surface. Fluid droplet 10A has a high capillary permeation that corresponds to a contact angle $\Phi_1$, which is less than about 90°. In contrast, FIG. 3B illustrates a fluid droplet 10B on solid substrate 12, having a low capillary permeation that corresponds to a contact angle $\Phi_2$, which is greater than about 90°. The wetting fluid, typically, should have a viscosity not greater than about 50 centipoise at room temperature, narrowly about 0.3 to about 5 centipoise, more narrowly about 0.4 to about 2.5 centipoise. The wetting fluid, accordingly, when added to the composition, reduces the viscosity of composition.

The wetting fluid should be mutually compatible with the polymer and the solvent and should not precipitate the polymer. The wetting fluid can also act as the solvent. Useful examples of the wetting fluid include, but are not limited to, tetrahydrofuran (THF), dimethylformamide (DMF), 1-butanol, n-butyl acetate, dimethyl acetamide (DMAC), and mixtures and combinations thereof. By way of example and not limitation, the polymer can comprise from about 0.1% to about 35%, more narrowly from about 2% to about 20% by weight of the total weight of the composition; the solvent can comprise from about 19.9% to about 98.9%, more narrowly from about 58% to about 84% by weight of the total weight of the composition; the wetting fluid can comprise from about 1% to about 80%, more narrowly from about 5% to about 40% by weight of the total weight of the composition. The specific weight ratio of the wetting fluid depends on the type of wetting fluid employed and type of and the weight ratio of the polymer and the solvent. More particularly, tetrahydrofuran used as the wetting fluid can comprise, for example, from about 1% to about 44%, more narrowly about 21% by weight of the total weight of the solution. Dimethylformamide used as the wetting fluid can comprise, for example, from about 1% to about 80%, more narrowly about 8% by weight of the total weight of the solution. 1-butanol used as the wetting fluid can comprise, for example, from about 1% to about 33%, more narrowly about 9% by weight of the total weight of the solution. N-butyl acetate used as the wetting fluid can comprise, for example, from about 1% to about 34%, more narrowly about 14% by weight of the total weight of the solution. Dimethyl acetamide used as the wetting fluid can comprise, for example, from about 1% to about 40%, more narrowly about 20% by weight of the total weight of the solution.

Table 1 illustrates some examples of suitable combinations for the primer composition:

TABLE 1

| Polymer | Solvent | Wetting Fluid | Initiators |
|---|---|---|---|
| EVAL | DMSO | — | — |
| EVAL | DMSO | THF | — |
| polyester polyurethanes | dimethylformamide | — | — |
| polyester polyurethanes | dimethylformamide | DMAC | — |
| polycaprolactone | Chloroform | n-butyl acetate | — |
| polyacrylate polyurethane | ethyl acetate | — | benzophenone |
| polyacrylated polyurethane | ethyl acetate | — | 1-hydroxycyclohexyl phenyl ketone |
| polyethyleneamine | $H_2O$ | — | — |
| methacrylic acid copolymer | THF | — | — |
| ethylene vinylacetate (e.g., 40% vinyl acetate content) | methylethylketone | — | — |
| aminopropyltriethoxysilane | ethanol/water 95/5 blend (w/w) | — | — |
| (3-glydidoxypropyl) methyldiethoxysilane | toluene | — | — |
| tetra-iso-propyl titanate (e.g., 0.25% w/w in isopropanol) | isopropanol | — | — |
| tetra-n-butyl titanate (e.g., 0.1–5% w/w in ethyl acetate) | ethyl acetate | — | — |

Composition for the Active Ingredient Layer

The embodiments of the composition for an active ingredient-containing or reservoir layer are prepared by conventional methods wherein all components are combined, then blended. More particularly, a predetermined amount of a polymeric compound is added to a predetermined amount of a mutually compatible solvent or combination of solvents. The polymeric compound can be added at ambient pressure and under anhydrous atmosphere. If necessary, gentle heating and stirring and/or mixing can be employed to effect dissolution of the polymer into the solvent, for example 12 hours in a water bath at about 60° C.

The polymer chosen must be a polymer that is biocompatible and minimizes irritation to the vessel wall when the device is implanted. The polymer may be either a biostable or a bioabsorbable polymer. Bioabsorbable polymers that could be used include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoesters, polyanhydrides, poly(glycolic acid), poly(D,L-lactic acid), poly(glycolic acid-co-trimethylene carbonate), polyphosphoesters, polyphosphoester urethanes, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Ethylene vinyl alcohol is functionally a very suitable choice of polymer. The copolymer allows for good control capabilities over the release rate of the active ingredient. As a general rule, an increase in the amount of the ethylene comonomer content decreases the rate that the active ingredient is released from the copolymer matrix. The release rate of the active ingredient typically decreases as the hydrophilicity of the copolymer decreases. An increase in the amount of the ethylene comonomer content increases the overall hydrophobicity of the copolymer, especially as the content of vinyl alcohol is concomitantly reduced. It is also known that the release rate and the cumulative amount of the active ingredient that is released are directly proportional to the total initial content of the ingredient in the copolymer matrix. Accordingly, a wide spectrum of release rates can be achieved by modifying the ethylene comonomer content and the initial amount of the active ingredient.

The choice of polymer for the reservoir layer can be the same as or different from the selected polymer for the primer layer. The use of the same polymer significantly reduces or eliminates any interfacial incompatibilities, such as lack of an adhesive tie or bond, which may exist with the employment of two different polymeric layers.

The solvent should be capable of placing the polymer into solution at the concentration desired in the solution. Examples of solvent can include, but are not limited to, DMSO, chloroform, water (buffered saline), xylene, acetone, methanol, ethanol, 1-propanol, tetrahydrofuran, 1-butanone, dimethylformamide, dimethylacetamide, cyclohexanone, and N-methyl pyrrolidinone. With the use of low ethylene content, e.g., 29 mol %, ethylene vinyl alcohol copolymer, a suitable choice of solvent is iso-propylalcohol (IPA) admixed with water.

Sufficient amounts of an active ingredient are dispersed in the blended composition of the polymer and the solvent. The active ingredient should be in true solution or saturated in the blended composition. If the active ingredient is not completely soluble in the composition, operations including mixing, stirring, and/or agitation can be employed to effect homogeneity of the residues. The active ingredient may be added so that the dispersion is in fine particles. The mixing of the active ingredient can be conducted in an anhydrous atmosphere, at ambient pressure, and at room temperature such that supersaturating the active ingredient is not desired.

The active ingredient should inhibit the activity of vascular smooth muscle cells. More specifically, the active ingredient is aimed at inhibiting abnormal or inappropriate migration and/or proliferation of smooth muscle cells.

"Smooth muscle cells" include those cells derived from the medial and adventitial layers of the vessel which proliferate in intimal hyperplastic vascular sites following vascular trauma or injury. Under light microscopic examination, characteristics of smooth muscle cells include a histological morphology of a spindle shape with an oblong nucleus located centrally in the cell with nucleoli present and myofibrils in the sarcoplasm. Under electron microscopic examination, smooth muscle cells have long slender mitochondria in the juxtanuclear sarcoplasm, a few tubular elements of granular endoplasmic reticulum, and numerous clusters of free ribosomes. A small Golgi complex may also be located near one pole of the nucleus.

"Migration" of smooth muscle cells means movement of these cells in vivo from the medial layers of a vessel into the intima, such as may also be studied in vitro by following the motion of a cell from one location to another, e.g., using time-lapse cinematography or a video recorder and manual counting of smooth muscle cell migration out of a defined area in the tissue culture over time.

"Proliferation" of smooth muscle cells means increase in cell number.

"Abnormal" or "inappropriate" proliferation means division, growth or migration of cells occurring more rapidly or to a significantly greater extent than typically occurs in a normally functioning cell of the same type, i.e., hyperproliferation.

"Inhibiting" cellular activity means reducing, delaying or eliminating smooth muscle cell hyperplasia, restenosis, and vascular occlusions, particularly following biologically or mechanically mediated vascular injury or trauma or under conditions that would predispose a mammal to suffer such a vascular injury or trauma. As used herein, the term "reducing" means decreasing the intimal thickening that results from stimulation of smooth muscle cell proliferation. "Delaying" means retarding the progression of the hyperproliferative vascular disease or delaying the time until onset of visible intimal hyperplasia, as observed, for example, by histological or angiographic examination. "Elimination" of restenosis following vascular trauma or injury means completely "reducing" and/or completely "delaying" intimal hyperplasia in a patient to an extent which makes it no longer necessary to surgically intervene, i.e., to re-establish a suitable blood flow through the vessel by, for example, repeat angioplasty, atherectomy, or coronary artery bypass surgery. The effects of reducing, delaying, or eliminating restenosis may be determined by methods known to one of ordinary skill in the art, including, but not limited to, angiography, intravascular ultrasound, fluoroscopic imaging, fiber optic visualization, optical coherence tomography, intravascular MRI, or biopsy and histology. Biologically mediated vascular injury includes, but is not limited to, injury caused by or attributed to autoimmune disorders, alloimmune related disorders, infectious disorders including endotoxins and herpes viruses such as cytomegalovirus, metabolic disorders such as atherosclerosis, and vascular injury resulting from hypothermia and irradiation. Mechanically mediated vascular injury includes, but is not limited to, vascular injury caused by catheterization procedures or vascular scraping procedures such as percutaneous transluminal coronary angioplasty, vascular surgery, stent placement, transplantation surgery, laser treatment, and other invasive procedures which disrupted the integrity of the vascular intima or endothelium. The active ingredient of the invention is not restricted in use for therapy following vascular injury or trauma; rather, the usefulness of the active ingredient will also be determined by the ingredient's ability to inhibit cellular activity of smooth muscle cells or inhibit the development of restenosis.

The active ingredient also includes any substance capable of exerting a therapeutic or prophylactic effect in the practice of the present invention as well as having positive pharmacological effects on the expression of the extracellular matrix. The active ingredient can also be for enhancing wound healing in a vascular site and improving the structural and elastic properties of the vascular site. Examples of such active ingredients include antiproliferative substances as well as antineoplastic, antiinflammatory, antiplatelet, anticoagulant, antifibrin, antithrombin, antimitotic, antibiotic, antioxidant, and combinations thereof. A suitable example of an antiproliferative substance includes actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Examples of suitable antineoplastics include paclitaxel and docetaxel. Examples of suitable antiplatelets, anticoagulants, antifibrins, and antithrombins include heparin, sodium heparin, low molecular weight heparin, heparin sulfate, heparin having a hydrophobic counterion, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include mannose-6-phosphate, superoxide dismutase, retinoic acid, suramin, asiaticoside, hyaluronan, alpha-interferon, genetically engineered epithelial cells, dexamethasone and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin. Exposure of the composition to the active ingredient is not permitted to adversely alter the active ingredient's composition or characteristic. Accordingly, the particular active ingredient is selected for mutual compatibility with the blended composition.

The dosage or concentration of the active ingredient required to produce a favorable therapeutic effect should be less than the level at which the active ingredient produces toxic effects and greater than the level at which non-therapeutic results are obtained. The dosage or concentration of the active ingredient required to inhibit the desired cellular activity of the vascular region can depend upon factors such as the particular circumstances of the patient; the nature of the trauma; the nature of the therapy desired; the time over which the ingredient administered resides at the vascular site; and if other bioactive substances are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

By way of example, the polymer can comprise from about 0.1% to about 35%, more narrowly from about 2% to about 20% by weight of the total weight of the composition, the solvent can comprise from about 59.9% to about 99.8%, more narrowly from about 79% to about 87% by weight of the total weight of the composition, and the active ingredient can comprise from about 0.1% to about 75%, more narrowly from about 20% to about 60% by weight of the total weight of the composition. Selection of a specific weight ratio of the polymer and solvent is dependent on factors such as, but not limited to, the material from which the device is made, the geometrical structure of the device, and the type and amount of the active ingredient employed. The particular weight percentage of the active ingredient mixed within the composition depends on factors such as duration of the release, cumulative amount of release, and release rate that is desired.

Optionally, a second fluid or solvent, such as tetrahydrofuran (THF) or dimethylformamide (DMF) can be used to improve the solubility of an active ingredient in the composition and/or to increase the wetting of the composition. Increasing the wetting of the composition has been discovered to lead to the application of a more uniformed coating.

The second fluid or solvent can be added to the composition or the active ingredient can be added to the second solvent prior to admixture with the blend.

With use of a second fluid, by way of example, the polymer can comprise from about 0.1% to about 35%, more narrowly from about 2% to about 20% by weight of the total weight of the composition, the solvent can comprise from about 19.8% to about 98.8%, more narrowly from about 49% to about 79% by weight of the total weight of the composition, the second solvent can comprise from about 1% to about 80%, more narrowly from about 5% to about 40% by weight of the total weight of the composition, and the active ingredient can comprise from about 0.1% to about 40%, more narrowly from about 1% to about 9% by weight of the total weight of the composition. Selection of a specific weight ratio of the polymer, the solvent, and the second solvent is dependent on factors such as, but not limited to, the material from which the implantable device is made, the geometrical structure of the device, and the type and amount of the active ingredient employed. The particular weight percentage of the active ingredient mixed within the composition depends on factors such as duration of the release, cumulative amount of release, and release rate that is desired.

Table 2 is an exemplary list of suitable combinations:

TABLE 2

| POLYMER | SOLVENT | SECOND SOLVENT | ACTIVE INGREDIENT |
| --- | --- | --- | --- |
| EVAL (29 mol % ethylene content e.g., Soarnol ®) | IPA/H$_2$O (1:1) | — | Actinomycin D |
| EVAL (44 mol % ethylene content) | DMSO | THF | Actinomycin D |
| EVAL | DMSO | THF | Actinomycin D |
| EVAL | DMSO | DMF | Paclitaxel |
| poly(L-lactic acid) | chloroform | — | dexamethasone |
| poly(lactic acid-co-glycolic acid) | acetone | — | dexamethasone |
| Polyether urethane | N-methyl pyrrolidinone | — | tocopherol |

Composition for the Rate Reducing Membrane

The embodiments of the composition for a rate-reducing membrane or diffusion barrier layer are prepared by conventional methods wherein all components are combined. In the embodiment with the use of particles, dispersion techniques should also be employed to circumvent agglomeration or formation of particle flocs.

More particularly, the composition for the barrier layer can be applied on a selected portion of the reservoir layer. The barrier layer can reduce the rate of release or delay the time at which the active ingredient is released from the reservoir region. In one embodiment, for maximum blood compatibility, polyethylene glycol or polyethylene oxide can also be added to the blend. Ethylene vinyl alcohol is functionally a very suitable choice of polymer. The copolymer allows for good control capabilities over the release rate of the active ingredient. As a general rule, an increase in the amount of the ethylene comonomer content decreases the rate that the active ingredient is released from the copolymer matrix. The release rate of the active ingredient decreases as the hydrophilicity of the polymer decreases. An increase in the amount of the ethylene comonomer content increases the overall hydrophobicity of the copolymer, especially as the content of vinyl alcohol is concomitantly reduced.

Usefully, the choice of polymer for the barrier layer can be the same as the selected polymer for the reservoir. The use of the same polymer can significantly reduce or eliminate interfacial incompatibilities, such as lack of adhesion, which may exist in the employment of two different polymeric layers.

Particles of inorganic or organic type can be added to the blend. The particles can be made from any suitable material having barrier-type properties, such as, but not limited to tortuousity, excluded volume, and adsorptivity. "Tortuosity" refers to the exclusion of space in the polymer matrix for the creation of a defined space or a tortuous path through and about which the active ingredient must travel to be expelled from the layer. "Excluded volume" refers to the volume displaced by the particles that would otherwise be available for the diffusion of the active ingredient. "Adsorptivity" refers to the chromatographic effect which is dependent upon the interaction between the active ingredient used in combination with the particle. The active ingredient may be partially adsorbed and released by the surface of the particles, such as silica or fumed carbon particles.

The particles should be dispersed in the blend. "Dispersed" is defined as the particles being present as individual particles, not agglomerates or flocs. In certain polymer-solvent blends, certain particles will disperse with ordinary mixing. Otherwise the particles can be dispersed in the composition by high shear processes such as ball mill, disc mill, sand mill, attritor, rotor stator mixer, ultrasonication—all such high shear dispersion techniques being well known to one of ordinary skill in the art. Optionally, one of the aforementioned wetting fluids can also be added to the blend. The wetting fluid can be added prior to, contemporaneously with, or subsequent to the agitation. Biocompatible dispersing agents in the form of surfactants, emulsifiers, or stabilizers may also be added to the blend to assist in particle dispersion.

The particles can be made from a metal oxide, such as rutile titanium oxide, anatase titanium dioxide, niobium oxide, tantalum oxide, zirconium oxide, iridium oxide, or tungsten oxide. In another embodiment, the particles can be made from a main group oxide such as silica (silicon oxide) or alumina (aluminum oxide). Metallic particles such as gold, hafnium, platinum, iridium, palladium, tungsten, tantalum, niobium, zirconium, titanium, aluminum, or chromium can also be employed. In another embodiment, carbonaceous particles made from, for example, lamp black, furnace black, carbon black, fumed carbon black, gas black, channel black, activated charcoal, diamond, diamond like carbon, or CVD diamond can be employed. In yet another embodiment, the particles can be made from nitrides such as titanium nitride, chromium nitride, and zirconium nitride. In yet another embodiment, carbides such as tungsten carbide, silicon carbide, or titanium carbide, and calcium salts such as hydroxyapatite, dahlite, brushite, tricalcium phosphate, calcium sulphate, and calcium carbonate can be used. Other inorganic particles can include particles made from silicides, barium titanate, and strontium titanate.

The particles can also be made from a suitable polymer including polymers of polyolefins, polyurethanes, cellulosics (i.e., polymers having mer units derived from cellulose), polyesters, polyamides, poly(hexamethylene isophthalamide/terephthalamide) (commercially available as SELAR PA™), poly(ethylene terephthalate-co-p-oxybenzoate) (PET/PHB, e.g., copolymer having about 60–80 mole percent PHB), poly(hydroxy amide ethers), polyacrylates, polyacrylonitrile, acrylonitrile/styrene copolymer (commercially available as LOPAC), rubber-modified acrylonitrile/acrylate copolymer (commercially available as BAREX), poly(methyl methacrylate), liquid crystal polymers (LCP) (e.g., VECTRA available from Hoescht-Celanese, ZENITE available from DuPont, and XYDAR available from Amoco Performance Chemicals), poly(phenylene sulfide), polystyrenes, polycarbonates, poly(vinyl alcohols), poly(ethylene-vinyl alcohol) (EVAL, e.g., having about 27 to about 47 mole percent of ethylene content), epoxies composed of bisphenol A based diepoxides with amine cure, aliphatic polyketones (e.g., CARILON available from Shell, and KETONEX available from British Petroleum), polysulfones, poly(ester-sulfone), poly(urethane-sulfone), poly(carbonate-sulfone), poly(3-hydroxyoxetane), poly(amino ethers), gelatin, amylose, parylene-C, parylene-D, parylene-N.

Representative polyolefins include those based upon alpha-monoolefin monomers having from about 2 to 6 carbon atoms and halogen substituted olefins, i.e., halogenated polyolefins. By way of example, and not limitation, low to high density polyethylenes, essentially unplasticized poly(vinyl chloride), poly(vinylidene chloride), poly(vinyl fluoride), poly(vinylidene fluoride), poly(tetrafluoroethylene) (Teflon), poly(chlorotrifluoroethylene) (KEL-F), and mixtures thereof are suitable. Low to high density polyethylenes are generally understood to have densities of about 0.92 g $cm^{-3}$ to about 0.96 g $cm^{-3}$, however, no bright line can be drawn for density classifications and the density can vary according to the supplier.

Representative polyurethanes include polyurethanes having a glass transition temperature above a storage or ambient temperature, for example having a glass transition temperature of at least 40° C. to 60° C., or having a non-polar soft segment which includes a hydrocarbon, silicone, fluorosilicone, or mixtures thereof. For example, ELAST-EON, manufactured by Elastomedic/CSIRO Molecular Science, is a polyurethane with a non-polar soft segment which is made from 1,4-butanediol, 4,4'-methylenediphenyl diisocyanate, and a soft segment composed of a blend poly(hexamethylene oxide) (PHMO) and bishydroxyethoxypropylpolydimethylsiloxane (PDMS). A useful example has a blend of 20% by weight PHMO and 80% by weight PDMS.

Representative examples of cellulosics include, but are not limited to, cellulose acetate having a degree of substitution (DS) greater than about 0.8 or less than about 0.6, ethyl cellulose, cellulose nitrate, cellulose acetate butyrate, methyl cellulose, and mixtures thereof.

Representative polyesters include saturated or unsaturated polyesters such as, but not limited to, poly(butylene terephthalate), poly(ethylene 2,6-naphthalene dicarboxylate) (PEN), and poly(ethylene terephthalate).

Representative polyamides include crystalline or amorphous polyamides such as, but not limited to, nylon-6, nylon-6,6, nylon-6,9, nylon-6,10, aromatic nylon MXD6 (manufactured by Mitsubishi Gas Chemical America, Inc.), and mixtures thereof.

Representative polyacrylates include, but are not limited to, poly(methylmethacrylate) and polymethacrylate.

The particle can be a mixture of the aforementioned polymers. For example, the polymer can comprise about 70% to about 99% by weight acrylonitrile and about 30% to about 1% by weight styrene. Similarly, copolymers of vinyl chloride and vinylidene chloride with a vinyl chloride content of about 1 to about 30 mole percent and PET/PHB copolymers with a PHB content of about 60 to about 80 mole percent function effectively.

Methods for Applying the Compositions to the Device

Before applying the primer layer, the surface of the device or prosthesis should be clean and free from contaminants that may be introduced during manufacturing. However, the surface of the prosthesis requires no particular surface treatment to retain the applied coating. Metallic surfaces of stents can be, for example, cleaned by argon plasma process as is well known to one of ordinary skill in the art. Application of the composition can be by any conventional method, such as by spraying the composition onto the prosthesis or immersing the prosthesis in the composition. Operations such as wiping, centrifugation, blowing, or other web clearing acts can also be performed to achieve a more uniform coating. Briefly, wiping refers to physical removal of excess coating from the surface of the stent; centrifugation refers to rapid rotation of the stent about an axis of rotation; and blowing refers to application of air at a selected pressure to the deposited coating. The excess coating can also be vacuumed off the surface of the device. The addition of a wetting fluid leads to a consistent application of the composition, which also causes the coating to be uniformly deposited on the surface of the prosthesis.

With the use of the thermoplastic polymers, such as EVAL, polycaprolactone, poly(lactide-co-glycolide), poly(hydroxybutyrate), etc., the deposited primer composition can be exposed to a heat treatment at a temperature range greater than about the glass transition temperature ($T_g$) and less than about the melting temperature ($T_m$) of the selected polymer. Unexpected results have been discovered with treatment of the composition under this temperature range, specifically strong adhesion or bonding of the coating to the metallic surface of a stent. The device should be exposed to the heat treatment for any suitable duration of time, which would allow for the formation of the primer coating on the surface of the device and allows for the evaporation of the solvent or combination of solvent and wetting fluid. It is understood that essentially all of the solvent and the wetting fluid will be removed from the composition but traces or residues can remain blended with the polymer.

Table 3 lists the $T_g$ and $T_m$ for some of the polymers used in the embodiments of the present invention. $T_g$ and $T_m$ of polymers are attainable by one of ordinary skill in the art. The cited exemplary temperature and time for exposure is provided by way of illustration and it is not meant to be limiting.

TABLE 3

| Polymer | $T_g$ (° C.) | $T_m$ (° C.) | Exemplary Temperature (° C.) | Exemplary Duration of Time For Heating |
|---|---|---|---|---|
| EVAL | 55 | 165 | 140 | 4 hours |
| Polycaprolactone | −60 | 60 | 50 | 2 hours |
| ethylene vinyl acetate (e.g., 33% vinylacetate content) | 36 | 63 | 45 | 2 hours |
| Polyvinyl alcohol | 75–85* | 200–220* | 165 | 2 hours |

*Exact temperature depends on the degree of hydrolysis which is also known as the amount of residual acetate.

With the use of one of the aforementioned thermoset polymers, the use of initiators may be required. By way of example, epoxy systems consisting of diglycidyl ether of bisphenol A resins can be cured with amine curatives, thermoset polyurethane prepolymers can be cured with polyols, polyamines, or water (moisture), and acrylated urethane can be cured with UV light. If baked, the temperature can be above the $T_g$ of the selected polymer.

With the use of the inorganic polymers, such as silanes, titanates, and zirconates the composition containing the prepolymer or precursor is applied and the solvent is allowed to evaporate.

As the primer layer is being applied or after the primer coating has been formed, the surface of the primer can be modified in order to increase the surface area of the primer. For instance, in one embodiment, asperities, or areas of roughness, are created on the surface of the primer layer. A variety of methods can be used to create the asperities on the primer layer covering the outer surface of the prosthesis. In one method, a pressurized stream of grit material is directed upon the polymeric primer coating after the primer layer has been dried. Examples of such processes include bead blasting and sand blasting. Bead blasting refers to the use of pressurized gas to project beads of a relatively uniform diameter at an object at a high velocity. The beads may be made of materials such as, but not limited to, aluminum oxide, silicon oxide, or latex. In sand blasting, the grit projected does not have as uniform diameter as in bead blasting. Both bead blasting and sand blasting are techniques that are well known to those of ordinary skill in the art. The roughness achieved using a pressurized grit source can be controlled by the size of the grit, e.g., the diameter of the beads, the pressure used, the distance between the grit source and the primer surface and the length of time the grit is blasted at the primer surface. By way of example and not limitation, the grit can be beads having a diameter of between 10 μm and 50 μm. Pressures of 30 PSI (pounds per square inch) to 60 PSI can be used to project the beads from a distance of approximately 3 to 10 cm from the stent.

Laser etching can also be used to create asperities or pores on the primer coating after the primer layer has been dried. Laser lithographic methods are known to those of ordinary skill in the art. A laser is directed onto the primer coating for a predetermined period of time, which depends on the etch rate and the depth of etch desired. A patterned mask that has openings may be applied over the primer coating before the laser is utilized. The laser is then allowed to etch the primer through the openings of the mask. The use of patterned masks with laser etchings is known to those of ordinary skill in the art.

In addition, the manner in which the primer is deposited onto the outer surface of the stent can create the asperities. The primer may be added via physical deposition processes, for example, by sputtering. Process conditions in which a lower pressure and shorter deposition time than is typically used for thin film deposition are used to form the asperities in the primer coating.

In addition, the surface of the primer coating can be modified by using a method to form a porous matrix. A porous matrix for the primer coating can be provided, for example, by phase inversion precipitation of a portion of the polymer in the primer layer. By way of example, a polymer is mixed with two miscible solvents to form a solution. One of the solvents (solvent A) should be less volatile than the other solvent (solvent B). Additionally, the polymer should be less soluble in solvent A. The solution can then be applied to a portion of the surface of the implantable device. Next, when the solvents are allowed to evaporate, the polymer slowly precipitates as solvent B is essentially removed from the coating. As a result, after complete drying, the polymer matrix becomes porous. One of ordinary skill in the art will understand that the size of the pores can be controlled by the choice of polymers and solvents and the relative concentrations of the solutions. The depth of porous matrix into the primer region can be controlled by only using the phase inversion technique after a portion of the primer layer has been applied to the surface of the stent. Pores in the range of about 0.1 microns to about 1 micron in diameter may be suitable.

The porous matrix in the primer layer can also be formed by using porogens. For example, a porogen can be added to the primer composition as monodispersed particles to create a porogen suspension. The porogen particles can comprise from about 5% to about 50% by weight of the total weight of the primer composition. The size of the porogen particles can be about 0.1 microns to 2 microns. The composition can then be applied to the device and after the layer is formed, the porogens can be dissolved away with an appropriate solvent, leaving cavities or pores in the primer layer to form the porous matrix. Representative examples of porogen particles include sodium chloride and glycine spheres. Usefully, the appropriate solvent is a compatible solvent for the porogen, but does not substantially dissolve the polymer used to form the primer layer. Water is a representative example of an appropriate solvent if sodium chloride or glycine spheres are used as the porogen.

The porous matrix can also be formed by using a sintering process. Sintering is a process of fabrication where particles are bonded together by partially melting some of the particles. For example, a polymeric powder or particles can be applied to the surface of the device and then pressed together. The particles can usefully be about 1 micron to about 10 microns. Then, the polymeric particles can be heated to temperatures slightly below or about the melting point of the polymer. Without entirely melting all of the particles, the particles bond to each other at their respective surfaces. Space remains between the lattice of the particles to form porous cavities.

Subsequent to the application of the primer layer, the composition containing the active ingredient (i.e., reservoir layer) can be applied to a designated portion of the primer coating. Masking techniques can be implemented for applying compositions containing different active ingredients to selected portions of the primer layer. Accordingly, stents having various cocktail formulations or combinations of a variety of active ingredients can be manufactured. The solvent(s) or the combination of the solvent(s) and the wetting fluid is removed from the composition by allowing the solvent(s) or combination of the solvent(s) and the wetting fluid to evaporate. The evaporation can be induced by heating the device at a predetermined temperature for a predetermined period of time. For example, the device can be heated at a temperature of about 60° C. for about 12 hours to about 24 hours. The heating can be conducted in an anhydrous atmosphere and at ambient pressure and should not exceed the temperature which would adversely affect the active ingredient. The heating can, alternatively, be conducted under a vacuum condition. It is understood that essentially all of the solvent and the wetting fluid will be removed from the composition containing the active ingredient but traces or residues can remain blended with the polymer.

A diffusion barrier layer can also be applied on a designated portion of the active ingredient-containing coating subsequent to the evaporation of the solvent(s) or solvent (s)/wetting fluid and the drying of the polymer for the active ingredient-containing coating. The diffusion barrier layer can also be applied by spraying the composition onto the device or immersing the device in the composition. The above-described processes can be similarly repeated for the formation of the barrier region.

Method of Use

In accordance with the above-described method, the active ingredient can be applied to a medical device, e.g., a stent, retained on the stent during delivery and expansion of the stent, and released at a desired control rate and for a predetermined duration of time at the site of implantation. A stent having the above-described coating layers is useful for a variety of medical procedures, including, by way of example, treatment of obstructions caused by tumors in bile ducts, esophagus, trachea/bronchi and other biological passageways. A stent having the above-described coating layers is particularly useful for treating occluded regions of blood vessels caused abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries. The application of the present invention should not, however, be limited to stents such that the embodiments of the coating can be used with a variety of medical substrates.

Briefly, an angiogram is first performed to determine the appropriate positioning for stent therapy. Angiography is typically accomplished by injecting a radiopaque contrast agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above described coating regions may then be expanded at the desired area of treatment. A post insertion angiogram may also be utilized to confirm appropriate positioning.

EXAMPLES

The embodiments of the invention will be illustrated by the following set forth examples which are being given by way of illustration only and not by way of limitation. All parameters and data are not be construed to unduly limit the scope of the embodiments of the invention.

Example 1

Multi-Link™ stents (available from Guidant Corporation) were cleaned by placement in an ultrasonic bath of isopropyl alcohol solution for 10 minutes. The stents were dried and plasma cleaned in a plasma chamber. An EVAL solution was made with 1 gram of EVAL and 7 grams of DMSO, making an EVAL:DMSO ratio of 1:7. The mixture was placed in a warm water shaker bath at 60° C. for 24 hours. The solution was cooled and vortexed. The cleaned Multi-Link™ stents were dipped in the EVAL solution and then passed over a hot plate, for about 3–5 seconds, with a temperature setting of about 60° C. The coated stents were heated for 6 hours in an air box and then placed in an oven at 60° C., under vacuum condition, and for 24 hours. The coated stents were expanded on a 4.0 mm angioplasty balloon. The coatings remained intact on the stents. The coatings were transparent giving the Multi-Link™ stents a glossy-like shine.

Example 2

Multi-Link™ stents were cleaned by placement in an ultrasonic bath of isopropyl alcohol solution for 10 minutes. The stents were dried and plasma cleaned in a plasma chamber. An EVAL solution was made with 1 gram of EVAL and 4 grams of DMSO, making an EVAL:DMSO ratio of 1:4. Dexamethasone was added to the 1:4 EVAL:DMSO solution. Dexamethasone constituted 9% by weight of the total weight of the solution. The solution was vortexed and placed in a tube. The cleaned Multi-Link™ stents were attached to mandrel wires and dipped into the solution. The coated stents were passed over a hot plate, for about 3–5 seconds, with a temperature setting of about 60° C. The coated stents were cured for 6 hours in an air box and then placed in a vacuum oven at 60° C. for 24 hours. The above-recited step was repeated twice. The average weight of the coating was 0.0003 gram, having an estimated dexamethasone content of 75 ug per stent. The coated stents were expanded on a 4.0 mm angioplasty balloon. The coatings remained intact on the stents. Verification of coverage and physical properties of the coatings were visualized using a scanning electron microscope. The coatings were transparent, giving the Multi-Link™ stents a glossy-like shine.

Example 3

Multi-Link Duet™ stents are cleaned by placement in an ultrasonic bath of isopropyl alcohol solution for 10 minutes. The stents are dried and plasma cleaned in a plasma chamber. The EVAL solution is made with 1 gram of EVAL and 4 grams of DMSO, making an EVAL:DMSO ratio of 1:4. Dexamethasone is added to the 1:4 EVAL:DMSO solution. Dexamethasone constitutes 9% by weight of the total weight of the solution. The solution is vortexed and placed in a tube. The cleaned Multi-Link™ stents are attached to mandrel wires and dipped into the solution. The coated stents are passed over a hot plate, for about 3–5 seconds, with a temperature setting of about 60° C. The coated stents are cured for 6 hours in an air box then placed in a vacuum oven at 60° C. for 24 hours. The single layered dexamethasone/EVAL coated stents are dipped into the 1:4 ratio EVAL:DMSO solution, free from dexamethasone. The stents are passed over the hot plate, cured, and placed in the oven as previously described. The top coating will provide a barrier layer for controlling the release of dexamethasone from the drug coated layer. The coated stents can be expanded on a 4.0 mm angioplasty balloon. It is predicted that the coatings will remain intact on the stents. The coatings will be transparent, giving the Multi-Link™ stents a glossy-like shine.

Example 4

Figure 4:
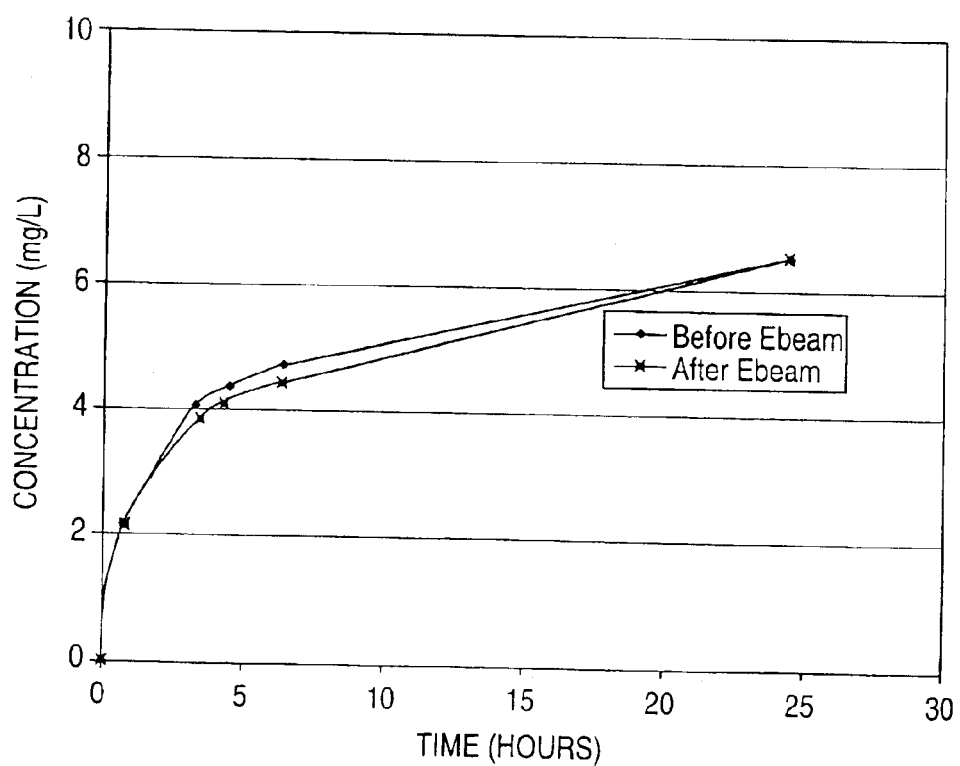
FIG. 4 graphically illustrates elution profiles for stents with a coating of ethylene vinyl alcohol copolymer impregnated with vinblastine as made according to Example 4.

Multi-Link™ stents were cleaned by placement in an ultrasonic bath of isopropyl alcohol solution for 10 minutes. The stents were dried and plasma cleaned in a plasma chamber. An EVAL solution was made with 1 gram of EVAL and 7 grams of DMSO, making an EVAL:DMSO ratio of 1:7. Vinblastine was added to the 1:7 EVAL:DMSO solution. Vinblastine constituted 2.5% by weight of the total weight of the solution. The solution was vortexed and placed in a tube. The cleaned Multi-Link™ stents were attached to mandrel wires and dipped into the solution. The coated stents were passed over a hot plate, for about 3–5 seconds, with a temperature setting of about 60° C. The coated stents were cured for 6 hours in an air box then placed in a vacuum oven at 60° C. for 24 hours. The above process was repeated twice, having a total of three layers. The average weight of the coating was 0.00005 gram, with an estimated vinblastine concentration of 12 microgram per stent. Some of the stents were sterilized by electron beam radiation. The sterilized and unsterilized vinblastine coated stents were tested for a 24 hour elution period by placing one sterilized and one unsterilized stent in 5 ml of phosphated saline solution (pH 7.4) at room temperature with rotational motion. The amount of vinblastine eluted was evaluated by High Performance Liquid Chromatography (HPLC) analysis. The results of this test are given below and plotted in FIG. 4. The data indicates that electron beam radiation procedure does not interfere in the release of vinblastine from EVAL.

| Time (Hours) | Microgram Released | Total Microgram Released | Microgram Release Per Hour |
|---|---|---|---|
| uz,7/26 Release Profile for Vinblastine - Unsterilized | | | |
| 0 | 0 | 0 | 0 |
| 0.5 | 2.12 | 2.12 | 4.24 |
| 3 | 1.91 | 4.03 | 0.76 |
| 4 | 0.27 | 4.30 | 0.27 |
| 6 | 0.38 | 4.68 | 0.19 |
| 24 | 1.7 | 6.38 | 0.09 |
| uz,7/26 Release Profile for Vinblastine - Sterilized | | | |
| 0 | 0 | 0 | 0 |
| 0.5 | 2.14 | 2.14 | 4.28 |
| 3 | 1.7 | 3.84 | 0.68 |
| 4 | 0.28 | 4.12 | 0.28 |
| 6 | 0.26 | 4.38 | 0.13 |
| 24 | 2.05 | 6.43 | 0.11 |

Example 5

Multi-Link™ stents were cleaned by placement in an ultrasonic bath of isopropyl alcohol solution for 10 minutes. The stents were dried and plasma cleaned in a plasma chamber. An EVAL solution was made with 1 gram of EVAL and, 7 grams of DMSO, making an EVAL:DMSO ratio of 1:7. Cephalotaxin was added to the 1:7 EVAL:DMSO solution. Cephalotaxin constituted 5% by weight of the total weight of the solution. The solution was vortexed and placed in a tube. The cleaned Multi-Link™ stents were attached to mandrel wires and dipped into the solution. The coated stents were passed over a hot plate, for about 3–5 seconds, with a temperature setting of about 60° C. The coated stents were cured for 6 hours in an air box then placed in a vacuum oven at 60° C. for 24 hours. The above process was repeated twice, having a total of three layers. The average weight of the coating was 0.00013 gram, with an estimated cephalotaxin concentration of 33 ug. The stents were sterilized by electron beam radiation. Cephalotaxin/EVAL coated stents and EVAL-coated control stents were implanted in the coronary arteries of 4 pigs, generally in accordance to the procedure set forth in "Restenosis After Balloon Angioplasty-A Practical Proliferative Model in Porcine Coronary Arteries" by Robert S. Schwartz, et al., Circulation 82(6):2190–2200, December 1990, and "Restenosis and the Proportional Neointimal Response to Coronary Artery Injury: Results in a Porcine Model" by Robert S. Schwartz et al., J Am Coll Cardiol; 19:267–74 February 1992. Results of the porcine artery study indicated that there was no significant difference between the uncoated, EVAL coated and cephalotaxin coated stents in the amount of neointimal proliferation resulting from arterial injury.

Example 6

Multi-Link Duet™ stents (available from Guidant Corporation) were cleaned by placement in an ultrasonic bath of isopropyl alcohol solution for 20 minutes, then air dried. An EVAL stock solution was made with 1 gram of EVAL and 7 grams of DMSO, making an EVAL:DMSO ratio of 1:7. The mixture was placed in a warm water shaker bath at 60° C. for 12 hours. The solution was mixed, then cooled to room temperature. A co-solvent was added to the EVAL solution to promote wetting of the struts of the Multi-Link Duet™ stents. One gram of tetrahydrofuran (THF) was mixed with 1.2 grams of the EVAL:DMSO solution. The cleaned Multi-Link Duet™ stents were attached to mandrel wires and dipped into the solution. The coated stents were passed over a hot plate, for about 3 to 5 seconds, with a temperature setting of about 60° C. The coated stents were then heated in a laboratory oven at 90° C. for 4 hours. The thin EVAL coating adhered to stainless steel without peeling or cracking. EVAL forms a superior primer base coat for other polymers that do not adhere well to stainless steel.

Example 7

Multi-Link Duet™ stents were cleaned in an ultrasonic bath of isopropyl alcohol for 20 minutes, then air dried. An EVAL solution was made with 1 gram of EVAL and 5 grams of DMSO, making an EVAL:DMSO ratio of 1:5. The mixture was placed in a warm water-shaker bath at 60° C. for 12 hours. The solution was mixed, then cooled to room temperature. The dissolved EVAL:DMSO solution was mixed with 24.6 grams of THF and 19.56 grams of DMSO. The solution was mixed then placed in the reservoir of an air pressured atomizing sprayer. Multi-Link Duet™ stents were sprayed while the stents rotated between 30 to 120 rpm. The spray time was dependent upon the flow rate of the sprayer. A flow rate between 1 to 20 mg/second required a stent to be sprayed between 1 to 30 seconds. The polymer coated Multi-Link Duet™ stents were heated in a forced air convection oven for 12 hours. The coatings were transparent, giving the Multi-Link Duet™ stents a glossy-like shine.

Example 8

Multi-Link Duet™ stents were cleaned in an ultrasonic bath of isopropyl alcohol for 20 minutes, then air dried. An EVAL stock solution was made having an EVAL:DMSO ratio of 1:4. The mixture was placed in a warm water shaker bath at 60° C. for 12 hours. The solution was mixed, then cooled to room temperature. Various co-solvents were examined to determine which co-solvent would promote a thicker coating. These co-solvents were THF, DMF, 1-butanol, and n-butyl acetate. The formulation for the co-solvents was as follows. Three grams of dissolved EVAL:DMSO solution was mixed with 0.9 gram of THF; three grams of dissolved EVAL:DMSO solution was mixed with 0.39 gram of DMF; three grams of dissolved EVAL:DMSO solution was mixed with 0.5 gram of 1-butanol; and three grams of dissolved EVAL:DMSO solution was mixed with 0.68 gram of n-butyl acetate. The cleaned Multi-Link Duet™ stents, attached to mandrel wires, were dipped into the solutions. The coated stents were passed over a hot plate, for about 3 to 5 seconds, with a temperature setting of about 60° C. The coated stents were heated in a forced air convection oven for 24 hours. A second layer of coating was applied to coated Multi-Link Duet™ stents and the stents were heated in the same manner as above. No difference was seen between the stents coated with the various co-solvents (e.g., greater weight of coating or physical appearance). All coated stents were transparent, giving the Multi-Link Duet™ stents a glossy-like shine. No webbing or bridging of the coating was seen between the struts of the coated Multi-Link Duet™ stents. The weight of the coatings was between 0.2 to 0.27 mg/stent.

Example 9

Multi-Link Duet™ stents are cleaned in an ultrasonic bath of isopropyl alcohol for 20 minutes, then air dried. An EVAL stock solution is made having an EVAL:DMSO ratio of 1:4. The mixture is placed in a warm water shaker bath at 60° C. for 12 hours. The solution is mixed, then cooled to room temperature. A 9% by weight Dexamethasone solution is formulated as follows: 2.96 grams of the EVAL:DMSO solution is mixed with 0.29 gram of Dexamethasone, then 0.9 gram of THF is added. The cleaned Multi-Link Duet™ stents are attached to mandrel wires and dipped into the solution. The coated stents are passed over a hot plate, for about 3 to 5 seconds, with a temperature setting of about 60° C. The coated stents are cured in a forced air convection oven for 2 hours. A second layer of coating is applied and cured in the above manner. It is predicted that the coatings will be transparent, giving the Multi-Link Duet™ stents a glossy-like shine.

Example 10

Multi-Link Duet™ stents are cleaned in an ultrasonic bath of isopropyl alcohol for 20 minutes, then air dried. An EVAL stock solution is made having an EVAL:DMSO ratio of 1:4. The mixture is placed in a warm water shaker bath at 60° C. for 12 hours. The solution is mixed, then cooled to room temperature. A 9% by weight Dexamethasone solution is formulated as follows: 2.96 grams of the EVAL:DMSO solution is mixed with 0.29 gram of Dexamethasone, then 0.9 gram of THF is added. The cleaned Multi-Link Duet™ stents are attached to mandrel wires and dipped into the solution. The coated stents are passed over a hot plate, for about 3 to 5 seconds, with a temperature setting of about 60° C. The coated stents are cured in a forced air convection oven for 2 hours. A second layer of coating is applied and cured in the above manner. It is predicted that the coatings will be transparent, giving the Multi-Link Duet™ stents a glossy-like shine.

Example 11

Multi-Link Duet™ stents were cleaned in an ultrasonic bath of isopropyl alcohol for 20 minutes, then air dried. An EVAL stock solution was made having an EVAL:DMSO ratio of 1:4. The mixture was placed in a warm water shaker bath at 60° C. for 12 hours. The solution was mixed, then cooled to room temperature. A 4.75% by weight actinomycin D solution was formulated as follows: 600 milligrams of the EVAL:DMSO solution was mixed with 40 milligrams of actinomycin D, then 200 milligrams of THF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 12

Multi-Link Duet™ stents were cleaned in an ultrasonic bath of isopropyl alcohol for 20 minutes, then air dried. An EVAL stock solution was made having an EVAL:DMSO ratio of 1:4. The mixture was placed in a warm water shaker bath at 60° C. for 12 hours. The solution was mixed, then cooled to room temperature. A 3.60% by weight actinomycin D solution was formulated as follows: 600 milligrams of the EVAL:DMSO solution was mixed with 40 milligrams of actinomycin D, then 480 milligrams of DMF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 13

Multi-Link Duet™ stents were cleaned in an ultrasonic bath of isopropyl alcohol for 20 minutes, then air dried. An EVAL stock solution was made having an EVAL:DMSO ratio of 1:4. The mixture was placed in a warm water shaker bath at 60° C. for 12 hours. The solution was mixed, then cooled to room temperature. A 6.45% by weight actinomycin D solution was formulated as follows: 680 milligrams of the EVAL:DMSO solution was mixed with 80 milligrams of actinomycin D, then 480 milligrams of DMF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 14

Multi-Link Duet™ stents are cleaned in an ultrasonic bath of isopropyl alcohol for 20 minutes, then air dried. An EVAL stock solution is made having an EVAL:DMSO ratio of 1:40. The mixture is placed in a warm water shaker bath at 60° C. for 12 hours. The solution is mixed, then cooled to room temperature. A 0.60% by weight actinomycin D solution can be formulated as follows: 4920 milligrams of the EVAL:DMSO solution is mixed with 40 milligrams of Actinomycin D, then 2000 milligrams of THF is added. The cleaned Multi-Link Duet™ stents can be sprayed upon by the above formulation. The coated stents are cured in a forced air convection oven for 2 hours. A second layer of coating is applied and cured in the above manner.

Example 15

Inhibition of SMC Proliferation with Actinomycin D

Figure 5:
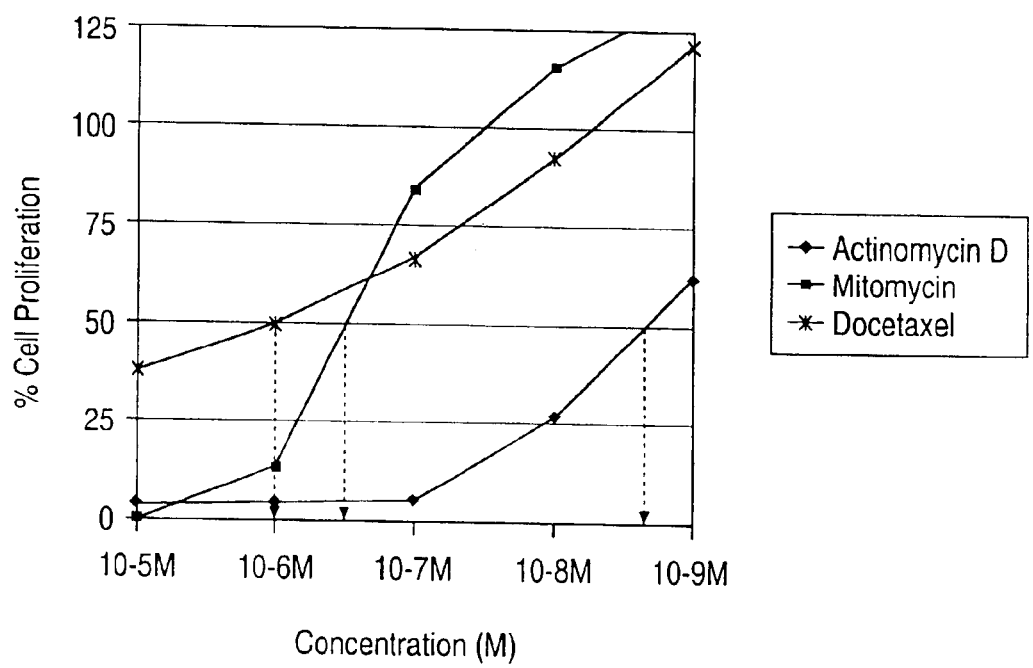
FIG. 5 graphically illustrates in vitro experimental data, in accordance with Example 15, showing affects of actinomycin D, mitomycin, and docetaxel on smooth muscle cell proliferation.

Medial smooth muscle cells (SMC) were isolated from rat aorta and cultured according to explant methods known to one of ordinary skill in the art. Cells were harvested via trypsinization and subcultivated. Cells were identified as vascular SMC through their characteristic hill-and-valley growth pattern as well as indirect immunofluorescence with monoclonal anti SMC α-actin. Studies were performed with cells at passage 3–4. SMC monoayers were established on 24 well culture dishes, scrape wounded and treated with actinomycin D, mytomycin and docetaxel. The cells were exposed to the drug solution of different concentrations for 2 hours and then washed with buffered saline solution. The proliferation of the cells was quantified by standard technique of thymidine incorporation. The results from the study are tabulated in FIG. 5.

The $IC_{50}$ (concentration at which 50% of the cells stop proliferating) of actinomycin D was $10^{-9}M$ as compared to $5\times10^{-5}$M for mitomycin and $10^{-6}$M for docetaxel. Actinomycin D was the most potent agent to prevent SMC proliferation as compared to other pharmaceutical agents.

Example 16

Reduction in Restenosis in the Porcine Coronary Artery Model

Porcine coronary models were used to assess the degree of the inhibition of neointimal formation in the coronary arteries of a porcine stent injury model by Actinomycin D, delivered with a microporous balloon catheter ($1\times16^6$ pores/mm$^2$ with sizes ranging from 0.2–0.8 micron).

The preclinical animal testing was performed in accordance with the NIH Guide for Care and Use of Laboratory Animals. Domestic swine were utilized to evaluate effect of the drug on the inhibition of the neointimal formation. Each testing procedure, excluding the angiographic analysis at the follow-up endpoints, was conducted using sterile techniques. During the study procedure, the activated clotting time (ACT) was monitored regularly to ensure appropriate anticoagulation. Base line blood samples were collected for each animal before initiation of the procedure. Quantitative coronary angiographic analysis (QCA) and intravascular ultrasound (IVUS) analysis was used for vessel size assessment.

The vessels at the sites of the delivery were denuded by inflation of the PTCA balloons to 1:1 balloon to artery ratio and moving the balloons back and forth 5 times. The drug was delivered to the denuded sites at 3.5 atm (3.61 Kg/sq cm) for 2 minutes using the microporous balloon catheters before stent deployment. The average volume of delivery was about 3.3+/−1.2 ml. Following drug delivery, stents were deployed at the delivery site such that final stent to artery ratio was 1.1:1.

QCA and IVUS analyses were used for stent deployment guidance. Pre-stenting IVUS measurements of the lumen size at the targeted vessel sites were performed for determination of the balloon (size) inflation pressure. Quantitative analysis of the stented coronary arteries to compare pre-stenting, post-stenting, follow-up minimal luminal diameters, stent recoil, and balloon/stent to artery ratio were performed. Following stent implantation and final angiogram, all devices were withdrawn and the wounds closed; the animals were allowed to recover from anesthesia as managed by the attending veterinarian or animal care professionals at the research center.

Upon return to the research laboratory at the 28-day endpoint, angiographic assessments were performed. Coronary artery blood flow was assessed and the stented vessels were evaluated to determine minimal lumen diameter. The animals were euthanized following this procedure at the endpoint. Following euthanasia, the hearts were pressure perfusion fixed with formalin and prepared for histological analysis, encompassing light microscopy, and morphometry. Morphometric analysis of the stented arteries included assessment of the position of the stent struts and determination of vessel/lumen areas, percent (%) stenosis, injury scores, intimal and medial areas and intima/media ratios. Percent stenosis is quantitated by the following equation:

$$100(IEL\ \text{area} - \text{lumen area})/IEL\ \text{area}$$

where IEL is the internal elastic lamia.

The control group of animals received delivery of water instead of the drug. The test group of animals received actinomycin D in two different concentrations of $10^{-5}$M and $10^{-4}$M. The results of the study are tabulated in Table 4. The percent stenosis in the treated groups (32.3+/−11.7) was significantly decreased as compared to the control groups (48.8+/−9.8). FIGS. 6A and 6B illustrate sample pictures of the histology slides of the coronary vessels from the control and the Dose 1 group, respectively.

TABLE 4

|  | CONTROL 0M | DOSE 1 1E − 05M | DOSE 2 1E − 04M | t test (significant if $p < 0.05$) | |
|---|---|---|---|---|---|
|  | (n = 9) | (n = 10) | (n = 7) | p~ | p* |
| ANGIOGRAPHIC DATA (QCA) | | | | | |
| Percent Diameter Stenosis | 48.8 +/− 9.8 | 36.8 +/− 9.7 | 32.3 +/− 11.7 | 0.02 | 0.01 |
|  | CONTROL 0M | DOSE 1 1E − 05M | DOSE 2 1E − 04M | t test (significant if $p < 0.05$) | |
|  | (n = 27) | (n = 30) | (n = 21) | p~ | p* |
| HISTOMORPHOMETRIC DATA | | | | | |
| Percent Stenosis (IEL area-lumen area)/IEL area | 63.4 +/− 12.7 | 51.8 +/− 13.8 | 54.1 +/− 11.7 | 0.002 | 0.01 |
| Residual Lumen (Lumen area)/IEL area | 0.36 +/− 0.16 | 0.49 +/− 0.14 | 0.46 +/− 0.08 | 0.002 | 0.01 |

~comparison between control and Dose 1
*comparison between control and Dose 2

The results of the in vitro and in vivo standard test procedures demonstrate that actinomycin D is useful for the treatment of hyper-proliferative vascular disease. Specifically, actinomycin D is useful for the inhibition of smooth muscle cell hyperplasia, restenosis and vascular occlusion in a mammal, particularly occlusions following a mechanically mediated vascular trauma or injury.

Example 17

Multi-Link Duet™ stents (13 mm in length) were cleaned in an ultrasonic bath of isopropyl alcohol for 20 minutes, then air dried. An EVAL stock solution was made having an EVAL:DMSO ratio of 1:4. The mixture was placed in a warm water shaker bath at 60° C. for 12 hours. The solution was mixed, then cooled to room temperature. A 5.06% by weight actinomycin D solution was formulated as follows: 40 milligrams of actinomycin D was dissolved in 150 milligrams of THF, then 600 milligrams of the EVAL:DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 260 micrograms and an average actinomycin D loading of about 64 micrograms was achieved.

Example 18

Multi-Link Duet™ stents (13 mm in length) were cleaned in an ultrasonic bath of isopropyl alcohol for 20 minutes, then air dried. An EVAL stock solution was made having an EVAL:DMSO ratio of 1:4. The mixture was placed in a warm water shaker bath at 60° C. for 12 hours. The solution was mixed, then cooled to room temperature. A 3.75% by weight actinomycin D solution was formulated as follows: 60 milligrams of actinomycin D was dissolved in 310 milligrams of DMF, then 1.22 grams of EVAL:DMSO solution was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 270 micrograms with an average actinomycin D content of about 51 micrograms was achieved.

Example 19

Multi-Link Duet™ stents were cleaned in an ultrasonic bath of isopropyl alcohol for 20 minutes, then air dried. An EVAL stock solution was made having an EVAL:DMSO ratio of 1:4. The mixture was placed in a warm water shaker bath at 60° C. for 12 hours. The solution was mixed, then cooled to room temperature. A 6.1% by weight actinomycin D solution was formulated as follows: 100 milligrams of actinomycin D was dissolved in 310 milligrams of DMF, then 1.22 grams of EVAL:DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 250 micrograms and an average actinomycin D loading of about 75 micrograms was achieved.

Example 20

Multi-Link Duet™ stents are cleaned in an ultrasonic bath of isopropyl alcohol for 20 minutes, then air dried. An EVAL stock solution is made having an EVAL:DMSO ratio of 1:40. The mixture is placed in a warm water shaker bath at 60° C. for 12 hours. The solution is mixed, then cooled to room temperature. A 0.60% by weight actinomycin D solution can be formulated as follows: 4920 milligrams of the EVAL:DMSO solution is mixed with 40 milligrams of Actinomycin D, then 2000 milligrams of THF is added. The cleaned Multi-Link Duet™ stents can be sprayed upon by the above formulation. The coated stents are cured in a forced air convection oven 60° C. for 15 minutes. Additional layers of the coating are applied and cured in the above manner. The final curing step for the coated stents is conducted for about 4 hours.

Example 21

A stainless steel stent can be spray coated with a formulation of EVAL and a drug, as previously described in any of the above examples. A diffusion barrier composition can be formulated with 2 grams of EVAL blended with 20 grams of dimethylsulfoxide. 2.2 grams of fumed silica can be added and dispersed with a high shear process. With constant agitation, 50 grams of tetrahydrofuran and 30 grams of dimethylformamide are admixed with the blend. The stent, having the EVAL coating, can be immersed in the diffusion barrier composition to form a layer.

Example 22

A stainless steel stent can be spray coated with a formulation of EVAL and a drug, as previously described in any of the above examples. A diffusion barrier formulation can be made by dissolving 8 grams of EVAL into 32 grams of dimethylsulfoxide. To this are added 14 grams of rutile titanium dioxide and 7 grams more of dimethylsulfoxide. The particles can be dispersed using a ball mill. The final solution is diluted with 39 grams of tetrahydrofuran, added slowly with constant agitation. It is predicted that the diffusion barrier will reduce the rate at which the drug is released from the stent.

Example 23

A stainless steel stent can be coated with a formulation of EVAL and a drug, as previously described in any of the above examples. A diffusion barrier formulation can be made by dissolving 8 grams of EVAL in 32 grams of dimethylsulfoxide. 10.5 grams of solution precipitated hydroxyapatite can be added to the blend. The particles can be dispersed using a rotor stator mixer. With constant agitation, 30 grams of tetrahydrofuran can be added. The stent can be coated by immersion followed by centrifugation.

Examples 24

A stent can be coated with a formulation of EVAL and a drug, as previously described in any of the above examples. 8 grams of EVAL can be added 50 grams of dimethylsulfoxide and the polymer can be dissolved by agitation and heat. Four grams of lamp black can be added and dispersed in a ball mill. 60 grams of dimethyl sulfoxide and 110 grams of tetrahydrofuran are slowly added while stirring. The stent can be spray coated.

Example 25

A stent can be coated with a formulation of EVAL and a drug, as previously described in any of the above examples. Colloidal gold can be prepared by reduction of tetrachloroauric acid with sodium citrate in aqueous solution. The solution can be exchanged by rinsing with tetrahydrofuran. Eight grams of EVAL can be dissolved in 32 grams of dimethylsulfoxide. To this is added a solution of 77 grams of colloidal gold in 32 grams of tetrahydrofuran. The stent can be coated by a dip coating process.

Example 26

In vivo data is provided illustrated positive remodeling caused by the application of actinomycin D. Stents coated with EVAL impregnated with actinomycin D and a control group of stents coated with EVAL free from actinomycin D were implanted in porcine coronary arteries. The animals were sacrificed at the end of 28 days. The EEL area of the actinomycin D-loaded vessels was statistically significantly greater than the EEL area of the control vessels. The index of remodeling was 1.076 (8.54/7.94).

| Condition | Mean Area | Std. Dev. |
|---|---|---|
| IEL | | |
| Drug coated (Act-D in EVAL) | 7.47 | 0.89 |
| Control (EVAL) | 6.6 | 0.61 |
| p value | 0.0002 | Statistical significant difference |
| EEL (external elastic lamia) | | |
| Drug coated (Act-D in EVAL) | 8.54 | 0.87 |
| Control (EVAL) | 7.94 | 0.73 |
| p value | 0.014 | Statistical significant difference |

EEL Area (mm$^2$)

| ID # | Control | ID # | Actinomycin D | ID # | EVAL |
|---|---|---|---|---|---|
| 48 LCX d | 6.3966 | 63 LCX d | 7.4498 | 63 LAD d | 8.3037 |
| 48 LCX m | 7.4601 | 63 LCX m | 8.2509 | 63 LAD m | 8.8545 |
| 48 LCX p | 7.3063 | 63 LCX p | 7.7342 | 63 LAD p | 9.4698 |
| 49 LAD d | 8.5573 | 63 RCA d | 7.9207 | 64 LCX d | 7.8063 |
| 49 LAD m | 8.5187 | 63 RCA m | 6.9926 | 64 LCX m | 7.1117 |
| 49 LAD p | 6.6346 | 63 RCA p | 8.3883 | 64 LCX p | 7.2411 |
| 58 LAD d | 8.6078 | 65 LAD d | 7.8546 | 64 RCA d | 8.3383 |
| 58 LAD m | 8.1674 | 65 LAD m | 9.2545 | 64 RCA m | 8.0793 |
| 58 LAD p | 8.3775 | 65 LAD p | 9.2515 | 64 RCA p | 8.3652 |
| 59 LCA d | 8.3054 | 68 LAD d | 8.7854 | 65 LCX d | 6.4638 |
| 59 LCX m | 7.3713 | 68 LAD m | 9.5164 | 65 LCX m | 7.1493 |
| 59 LCX p | 7.8662 | 68 LAD p | 9.1504 | 65 RCA d | 8.5955 |
| 59 RCA d | 7.3714 | 69 LCX d | 9.6679 | 65 RCA m | 8.0855 |
| 59 RCA m | 6.6783 | 69 LCX m | 9.1237 | 65 RCA p | 8.4785 |
| 59 RCA p | 7.4707 | 69 LCX p | 9.9849 | 68 LCX d | 8.4723 |
| 62 LCX d | 7.8784 | 69 RCA d | 9.4765 | 68 LCX m | 7.8382 |
| 62 LCX m | 7.5318 | 69 RCA m | 7.4424 | 68 LCX p | 8.0570 |
| 62 LCX p | 6.2647 | 69 RCA p | 9.1462 | 68 RCA d | 8.4840 |
| 62 RCA d | 8.3240 | 70 LCX d | 8.9504 | 68 RCA p | 8.8767 |
| 62 RCA m | 7.9535 | 70 LCX m | 8.9117 | 69 LAD d | 6.6648 |
| 62 RCA p | 8.5454 | 70 LCX p | 8.7533 | 69 LAD m | 6.8614 |
| 67 LAD d | 8.9532 | 70 RCA d | 7.3249 | 69 LAD p | 7.7632 |
| 67 LAD m | 9.2410 | 70 RCA m | 7.1061 | 70 LAD d | 7.5175 |
| 67 LAD p | 8.3841 | 70 RCA p | 8.5830 | 70 LAD m | 7.8630 |
| | | | | 70 LAD p | 8.2222 |
| AVG | 7.8402 | | 8.5425 | | 7.9475 |
| SD | 0.8046 | | 0.8755 | | 0.7349 |

ActD vs EVAL

| P = | 0.014709 |
|---|---|
| AVG % EEL growth | 7.486304 |

IEL Area (mm$^2$)

| ID # | Control | ID # | Actinomycin D | ID # | EVAL |
|---|---|---|---|---|---|
| 48 LCX d | 5.2178 | 63 LCX d | 6.3785 | 63 LAD d | 6.9687 |
| 48 LCX m | 6.2108 | 63 LCX m | 7.5206 | 63 LAD m | 7.3908 |
| 48 LCX p | 6.1125 | 63 LCX p | 6.9992 | 63 LAD p | 7.3563 |
| 49 LAD d | 7.2848 | 63 RCA d | 6.9632 | 64 LCX d | 6.4420 |
| 49 LAD m | 7.4117 | 63 RCA m | 6.0418 | 64 LCX m | 6.0064 |
| 49 LAD p | 5.9918 | 63 RCA p | 7.4794 | 64 LCX p | 5.9970 |
| 58 LAD d | 7.2049 | 65 LAD d | 6.2324 | 64 RCA d | 6.8001 |
| 58 LAD m | 6.9334 | 65 LAD m | 8.3785 | 64 RCA m | 6.8561 |
| 58 LAD p | 6.9454 | 65 LAD p | 8.5819 | 64 RCA p | 7.0172 |
| 59 LCA d | 7.2640 | 68 LAD d | 8.0964 | 65 LCX d | 5.2485 |
| 59 LCX m | 6.2014 | 68 LAD m | 8.6879 | 65 LCX m | 6.1135 |
| 59 LCX p | 6.7283 | 68 LAD p | 8.0914 | 65 RCA d | 7.1525 |
| 59 RCA d | 6.0519 | 69 LCX d | 8.7181 | 65 RCA m | 6.4815 |
| 59 RCA m | 5.9992 | 69 LCX m | 8.0273 | 65 RCA p | 7.1775 |
| 59 RCA p | 5.9032 | 69 LCX p | 8.5222 | 68 LCX d | 6.9571 |
| 62 LCX d | 6.5329 | 69 RCA d | 8.3796 | 68 LCX m | 6.5724 |
| 62 LCX m | 6.2804 | 69 RCA m | 6.4219 | 68 LCX p | 6.7740 |
| 62 LCX p | 4.9303 | 69 RCA p | 7.7757 | 68 RCA d | 7.2425 |
| 62 RCA d | 7.0977 | 70 LCX d | 7.5392 | 68 RCA p | 7.5554 |
| 62 RCA m | 6.7466 | 70 LCX m | 7.6573 | 69 LAD d | 5.5505 |
| 62 RCA p | 7.1747 | 70 LCX p | 6.9749 | 69 LAD m | 5.5571 |
| 67 LAD d | 8.0264 | 70 RCA d | 6.2815 | 69 LAD p | 6.2697 |
| 67 LAD m | 8.1144 | 70 RCA m | 5.9760 | 70 LAD d | 6.3212 |
| 67 LAD p | 7.2091 | 70 RCA p | 7.6195 | 70 LAD m | 6.6518 |
| | | | | 70 LAD p | 6.9032 |
| AVG | 6.6489 | | 7.4727 | | 6.6025 |
| SD | 0.7883 | | 0.8972 | | 0.6130 |

ActD vs EVAL

| P = | 0.000283 |
|---|---|
| AVG % IEL growth | 13.17981 |

Figure 7B:
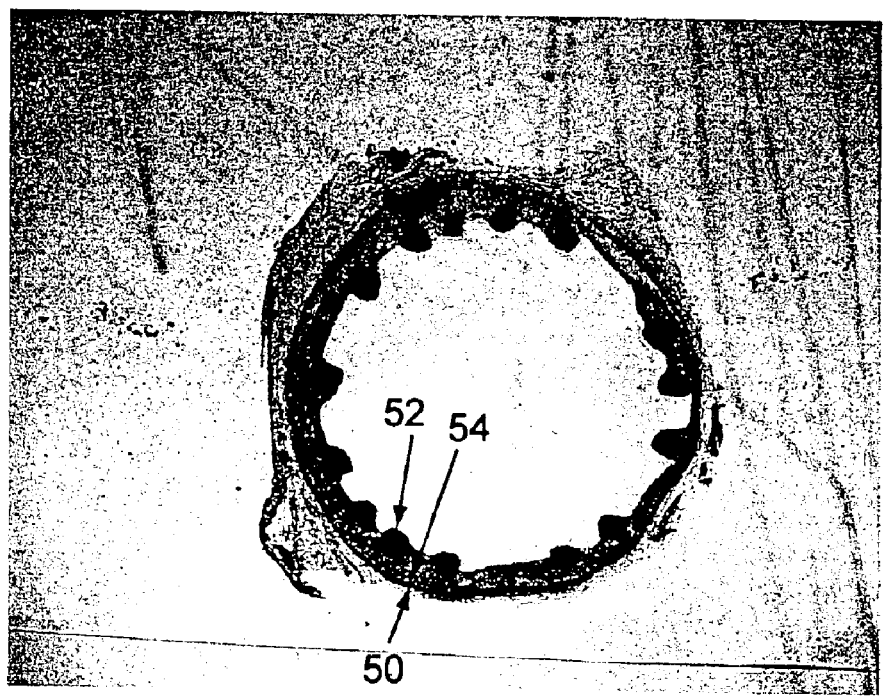
FIG. 7B is a picture of a histology slide of a coronary vessel from the actinomycin D group in accordance with Example 26.

FIGS. 7A and 7B illustrate sample pictures of the histology slides of the coronary vessels from the control group 64 RCA (Right Coronary Group) and the actinomycin D loaded stent group 68 LAD (Left Anterior Descending), respectively. The stent used was an Advanced Cardiovascular Systems Multi-Link Duet™ (stainless steel). As is illustrated by FIG. 7B, the positive remodeling of EEL 50, caused by the application of actinomycin D, creates a gap between stent struts 52 and EEL 50. Thrombus deposits, illustrated by reference number 54, are formed in the gap over time. The use of a self-expandable stent eliminates the formation of the gap as the stent self-expands in response to the positive remodeling of IEL. Thrombus deposits can be, accordingly, eliminated.

Actinomycin D induces the positive remodeling of the vessel walls, more particularly positive remodeling of the external elastic lamina (EEL) of a blood vessel wall. Positive remodeling is generally defined as the ability of the vessel walls to structurally adapt, by increasing in lumen size, to chronic stimuli. A positively remodeled lumen wall has a greater diameter or size as compared to a lumen wall which has not been subjected to the remodeling effect. Accordingly, the flow of blood through the remodeled site is increased—flow which would have otherwise been reduced because of, for example, the presence of plaque build-up or migration and proliferation of cells. The index of remodeling is defined by the ratio of the area circumscribed by the EEL of the lesion site to the area circumscribed by the EEL of a reference site. As a result of the positive remodeling of the EEL, the internal elastic lamina (IEL), in response, can also increases in area or diameter. Actinomycin D, or analogs or derivative thereof, not only can inhibit abnormal or inappropriate migration and/or proliferation of smooth muscle cells, which can lead to restenosis, but can also induce positive remodeling of the blood vessel walls. Thus the widening of the diseased region becomes more pronounced.

Example 27

2 grams of an acrylate terminated urethane (Henkel 12892) can be added to 18 grams of ethyl acetate with 0.08 grams of benzophenone and 0.08 grams of 1-hydroxycyclohexyl phenyl ketone. After application, the stent can be cured for 5 minutes under medium pressure mercury lamp.

Example 28

For a thermoset system, 1.67 grams of Epon 828 (Shell) resin can be added to 98 grams of propylene glycol monomethyl ether and 0.33 grams of Jeffamine T-430 (Huntsman). After application, the stent can be baked for 2 hours at 80° C. and 2 hours at 160° C.

Example 29

A 0.25% (w/w) solution of tetra-n-butyl titanate can be made in anhydrous ethyl acetate. The solution can be applied by spraying to a surface of a stainless steel stent. The stent can be heated at 100° C. for two hours.

Example 30

Objective

Coated stents tested through simulated delivery to a target lesion for testing the mechanical integrity of the coating.

| Group | Quantity | Coating |
| --- | --- | --- |
| A | 2 | Control: 2% EVAL in 1:1 THF:DMSO, 3:1 EVAL:Act-d; no primer |
| B | 2 | 2% EVAL in 5:3:2 THF:DMF:DMSO, 3:1 EVAL:Act-d; no primer |
| C | 2 | EVAL primer layer baked at 120 C./60 C. for 2/10 hrs + 2% EVAL in 1:1 THF:DMSO, 3:1 EVAL:Act-d; primer |
| D | 2 | EVAL primer layer baked at 140 C./60 C. for 2/2 hrs + 2% EVAL in 1:1 THF:DMSO, 3:1 EVAL:Act-d; primer |

Background

In this experiment four different treatment groups were tested through a simulated delivery and use. Number of peel defects at rings 3, 5, and 7, with a peel defect defined as a location on the stent where coating has been removed to expose bare stent or an underlying layer of coating, were observed.

Materials and Equipment 1. 8, 13 mm Solo stents (Available from Guidant Corporation);
2. 8, 3.0×30 mm Duet catheters;
3. 100% IPA;
4. Tominator Stent Crimper S/N 400;
5. 7F JL4 guiding catheter;
6. 0.014" Balance Middle Weight guide wire;
7. Rotating Hemostatic Valve; and
8. SVS tortuosity tree (2.5 mm lumen tapering to 1.5 mm lumen).

Preparation

Crimped the stents onto the catheters using the Tominator crimper and the following conditions: 3 crimps, 65 psi, rotation between crimps.

Test Procedure

1. Performed simulation using heart model having a tortuosity and contained in a tub filled with water.
    a. Inserted the stents through the following set-up: RHF, 7F JL4 guiding catheter, SVS tortuosity tree (2.5 mm lumen at entrance, 1.5 mm lumen at exit).
    b. Once the stent passed through the distal opening of tortuosity, the balloon was cut from the catheter just distal to proximal marker.
2. Examined the stents under 100× magnification using Leica MZFLIII microscope in the clean environment room (CER).
3. Recorded number of peel defects at stent rings 3, 5, and 7. Only the outer diameter ("OD") was examined for peel defects.
4. All test samples were handled with personal protective equipment (PPE) appropriate for drug containing stents.

Data Summary and Results

| Group | # Peel Defects/Ring | Comments |
| --- | --- | --- |
| A (THF) | 2.0 | — |
| B (DMF) | 5.3 | Began with poor coating finish. |
| C (140° C.) | 0.7 | — |
| D (120° C.) | 0 | — |

Discussion

The test was performed to observe the coating integrity after a simulated delivery to a tortuosity without a lesion. The primer layer improved coating adhesion to the stents that resulted in fewer defects after a simulated use. Group B had a number defects. Although the coating surface for Group B was poor to begin with, and the defects were not too severe.

Example 31

Objective

The adhesion of 0.67% Actinomycin-D (in 5% EVAL 1:1 THF:DMSO solution) coating on stents with two different surface treatments was compared to control samples. The specific surface treatments consisted of: (1) Argon plasma treatment; and (2) Argon plasma treatment with a primer layer of 5% EVAL in 1:1 DMSO:DMF solution applied with the dip-spin process, i.e., centrifugation process, and followed by heat treatments at 120° C. for two hours and 60° C. for 10 hours. The test method used to test adhesion of coatings on stents was a wet flow test, expanding the stents in Tecoflex tubing at 37° C. of water or saline. Water or saline is then flushed through the stents for 18 hours to simulate blood flow through the sterns. The stents were then removed from the Tecoflex with a "stent catcher" and observed under optical microscope for defects.

| Group | Treatment | Flow Rate |
| --- | --- | --- |
| A | None | 50 mL/min |
| B | Argon plasma | 50 mL/min |
| C | Argon plasma + 5% EVAL in 1:1 DMSO:DMF heated at 120° C. for two hours and 60° C. for 10 hours | 50 mL/min |
| D | None | 100 mL/min |
| E | Argon plasma | 100 mL/min |
| F | Argon plasma + 5% EVAL in 1:1 DMSO:DMF heated at 120° C. for two hours and 60° C. for 10 hours | 100 mL/min |

Materials and Equipment 1. 30, 13 mm coated Solo stents, cleaned ultrasonically in IPA for 15 minutes;
2. 30, balloon catheters or subassemblies to expand the stents (3.0×20 mm RX Rocket);

3. 0.67% Actinomycin-D in 5% EVAL with 1:1 THF:DMSO solution;
4. 5% EVAL in 1:1 DMF:DMSO;
5. 3.0 mm, thin walled Tecoflex tubing;
6. Saline;
7. Lint Free Wipes SU 00126 or equivalent;
8. 100% IPA;
9. Oven;
10. Timer;
11. Centrifuge;
12. Plasma Machine (available from Advanced Plasma System);
13. Ultrasonic cleaner;
14. Mettler balance with 0.1 micrograms resolution; and
15. Spray Coater with Fan Air Cap and EFD dispenser (EFD Inc. East Providence, R.I.).

Preparation
1. Sonicated the stents in IPA for 15 minutes;
2. Weighed each stent to the nearest microgram;
3. Prepared 5 stent samples:
   A. Groups A and D:
      i. Performed spray-coating process in CER under the following conditions: 3 passes, 3-second spray, no blowing.
      ii. Weighed each sample at the end of the last pass to the nearest microgram.
      iii. Baked the samples for 4 hrs at 60° C.
      iv. Placed the stents into the Tecoflex tubing with a balloon catheter—submerged in 37° C. saline.
   B. Groups B and E:
      i. Placed the samples on a sample holder. Performed argon plasma treatment using plasma machine.
      ii. Performed spray-coating process in CER under the following conditions: 3 passes, 3-second spray, no blow.
      iii. Weighed each sample at the end of the last pass to the nearest microgram.
      iv. Baked the samples for 4 hrs at 60° C.
      v. Placed the stents into the Tecoflex tubing with the balloon catheter—submerged in 37° C. saline.
   C. Groups C and F:
      i. Placed samples flat on a sample holder. Performed argon plasma treatment.
      ii. Used dip-spin process to apply 2% EVAL primer layer, 1:1 DMSO:DMF.
      iii. Baked the stents at 120° C. for two hours.
      iv. Baked the stents at 60° C. for ten hours.
      v. Performed spray-coating process in CER under the following conditions: 3 passes, 3-second spray, no blow.
      vi. Weighed each sample at the end of the last pass to the nearest microgram.
      vii. Baked the samples for 4 hrs at 60° C.
      viii. Placed the stents into the Tecoflex tubing with a balloon catheter—submerged in 37° C. water.

Test Procedure
Tested three samples from each group. Wet Flow Testing:
1. Expanded the stents into the 3.0 mm Tecoflex tubing in 37° C. saline.
2. Performed wet flow testing for 18 hrs.
3. Removed the stents from the Tecoflex tubing with a stent catcher.
4. Count defects, based on the following categories: Defect type; defect size; defect location; and peel defects on rings 3, 5, and 7.
5. Stent weight could not be a measurable because of the loss of the drug and uptake of water.
6. All test samples were handled with PPE appropriate for drug containing stents.

Data Summary

| Group | Average # of Peel Defects/Stent (3 rings) After Flow Test | Average # Peel Defects/Ring After Flow Test |
|---|---|---|
| A | 18.0 | 6.0 |
| B | 15.3 | 5.1 |
| C | 2.7 | 0.9 |
| D | 14.3 | 4.8 |
| E | 14.0 | 4.7 |
| F | 0.7 | 0.2 |

Discussion

Peel defects are defined as areas where the coating separated from the stent. The number of peel defects were counted on the stents' OD/sidewall on rings 3, 5, and 7. The flow field was on the inner diameter ("ID") of the stents' surface. Some of the damage to the OD surface could have been aggravated by the Tecoflex tubing. The number of peel defects observed on groups C and F (EVAL primer) was clearly lower than the other two test groups, regardless of flow rate. The increased flow rate did not induce more peel defects.

Example 32

Objective

The objective of this experiment was to test the adhesive properties of an Actinomycin-D containing coating on stainless steel stents having an EVAL primer layer. The coated stents were tested in a wet flow test condition of saline heated to 37° C. The number of "peel defects" on a select number of stent rings was observed. A "peel defect" is defined as a location on the stent surface devoid of coating, i.e., bare metal or underlying coating layer that is visible under optical magnification of less than 100×.

| Group | Treatment | Flow Rate |
|---|---|---|
| A | Argon plasma treatment + EVAL primer layer (15% EVAL, 1:1 DMF:DMSO) baked at 140° C. for 2 hours and dried at 60° C. for 2 hours | 50 mL/min |
| B Control | Argon plasma treatment + EVAL primer layer (15% EVAL, 1:1 DMF:DMSO) baked at 120° C. for 2 hours and dried at 60° C. for 10 hours | 50 mL/min |

Materials and Equipment
1. 10, 13 mm Solo stents, cleaned ultrasonically in IPA for 15 minutes;
2. 10, balloon catheters or subassemblies to expand the stents;
3. 15% EVAL in 1:1 DMF:DMSO solution;
4. Actinomycin-D solution, 1:1 THF:DMSO with 3:1 EVAL:Act-D;
5. Tecoflex tubing
6. Saline
7. Lint Free Wipes SU 00126 or equivalent
8. 100% IPA
9. Oven
10. Timer
11. Plasma Machine (Advanced Plasma System);

12. Ultrasonic cleaner; and
13. Mettler balance with 0.1 micrograms resolution.

Preparation

1. Sonicated the stents in IPA for 15 minutes.
2. Weighed each stent to the nearest microgram.
3. Prepared 5 stent samples for each group:
   A. Group A (Control):
      i. Placed the samples flat on a sample holder. Performed argon plasma treatment.
      ii. Used dip-spin process, i.e., centrifugation at 6000 rpm for one minute, to apply the EVAL primer layer, 1:1 DMSO:DMF.
      iii. Baked the stents at 140° C. for two hours in the convection oven.
      iv. Took weight measurements of each stent to the nearest microgram.
      v. Baked the stents at 60° C. for two hours in vacuum oven.
      vi. Took weight measurements of each stent to the nearest microgram.
      vii. Performed spray-coating process in CER under the following conditions: 3 passes, 3-second spray, no blow.
      viii. Weighed each sample at the end of the last pass to the nearest microgram.
      ix. Baked samples for 4 hrs at 60° C.
      x. Took weight measurements of each stent to the nearest microgram.
      xi. Placed the stents into the Tecoflex tubing with a balloon catheter—submerged in 37° C. water.
   B. Groups B:
      i. Placed samples flat on sample holder. Performed argon plasma treatment.
      ii. Used dip-spin process at 6000 rpm for one minute to apply EVAL primer layer, 1:1 DMSO:DMF.
      iii. Baked the stents at 120° C. for two hours in the convection oven.
      iv. Took weight measurements on each stent to the nearest microgram.
      v. Baked the stents at 60° C. for ten hours in vacuum oven.
      vi. Took weight measurements for each stent to the nearest microgram.
      vii. Performed spray-coating process in CER at the following conditions: 3 passes, 3-second spray, no blow.
      viii. Weighed each sample at the end of the last pass to the nearest microgram.
      ix. Baked the samples for 4 hrs at 60° C.
      x. Took weight measurements of each stent to the nearest microgram.
      xi. Placed the stents into the Tecoflex tubing with a balloon catheter—submerged in 37° C. water.

Test Procedure

1. Performed wet flow testing overnight for about 18 hrs.
2. Removed the stents from the Tecoflex tubing with a stent catcher.
3. Counted the defects based on the number of peel defects at rings 3, 5, and 7 on the stents' OD. Count the defects on the ID of the same rings.
4. The weight could not be measured because of the loss of the drug and uptake of water.
5. All test samples were handled with PPE appropriate for drug containing stents.

Data Summary and Results

| Group | # Peel Defects (OD) | Average # of Peel Defects/Ring (OD, rings 3, 5, 7) | # Peel Defects (ID) | Average # of Peel Defects/Ring (ID, rings 3, 5, 7) |
|---|---|---|---|---|
| A | 0 | 0 | 1 | 0.3 |
|   | 0 | 0 | 1 | 0.3 |
|   | 0 | 0 | 1* | 0.3 |
| B | 0 | 0 | 0 | 0 |
|   | 0 | 0 | 0 | 0 |
|   | 0 | 0 | 0 | 0 |

*Defect occurred at a location of a defect in the stent surface.

Example 33

Objective

The objective of this study was to test the adhesive properties of an Actinomycin-D containing coating on stainless steel stents having an EVAL primer layer. The coated stents were tested under wet flow conditions of saline heated to 37° C. The number of "peel defects" on a select number of stent rings was observed. A "peel defect" is defined as a location on the stent surface devoid of coating, i.e., bare metal or an underlying coating layer that is visible under optical magnification of no more than 100×.

| Group | Treatment | Flow Rate |
|---|---|---|
| A Control | None | 50 mL/min |
| B | Argon plasma treatment + EVAL primer layer by dip-spin (2% EVAL, 1:1 DMF:DMSO) baked at 140° C. for 4 hours | 50 mL/min |
| C | EVAL primer layer by dip-spin (2% EVAL, 1:1 DMF:DMSO) baked at 140° C. for 4 hours | 50 mL/min |
| D | Argon plasma treatment + EVAL primer layer by spray (2% EVAL, 1:1 DMF:DMSO) baked at 140° C. for 4 hours | 50 mL/min |
| E | EVAL primer layer by spray (2% EVAL, 1:1 DMF:DMSO) baked at 140° C. for 4 hours | 50 mL/min |

Materials and Equipment 1. 25, 13 mm Solo stents, cleaned ultrasonically in IPA for 15 minutes;
2. 25, balloon catheters or subassemblies to expand the stents;
3. 2% EVAL in 1:1 DMF:DMSO solution;
4. Actinomycin-D solution, 1:1 THF:DMSO with 3:1 EVAL:Act-D;
5. 3.0 mm Tecoflex tubing;
6. Saline;
7. Lint Free Wipes SU 00126 or equivalent;
8. 100% IPA;
9. Convection Oven
10. Timer;
11. Plasma Machine;
12. Ultrasonic cleaner; and
13. Mettler balance with 0.1 micrograms resolution.

Preparation

1. Sonicated the stents in IPA for 15 minutes.
2. Weighed each stent to the nearest microgram.
3. Prepared 5 stent samples for each group.
   A. Group A (Control):
      i. Performed spray-coating process in CER under the following conditions: 3 passes, 3-second spray, no blow.

ii. Weighed each sample at the end of the last pass to the nearest microgram.
iii. Baked the samples for 4 hrs at 60° C.
iv. Took the weight measurements of each stent to the nearest microgram.
v. Placed the stents into the Tecoflex tubing with the balloon catheter—submerged in 37° C. water.

B. Group B:
i. Placed samples flat on sample holder. Perform argon plasma treatment.
ii. Used dip-spin process to apply EVAL primer layer, 1:1 DMSO:DMF (6000 rpm for one minute).
iii. Baked the stents at 140° C. for 4 hours in convection oven.
iv. Took weight measurements on each stent to the nearest microgram.
v. Performed spray-coating process in CER at the following conditions: 3 passes, 3-second spray, no blow.
vi. Weighed each sample at the end of the last pass to the nearest microgram.
vii. Baked the samples for 4 hrs at 60° C.
viii. Took the weight measurements of each stent to the nearest microgram.
ix. Placed the stents into the Tecoflex tubing with a balloon catheter—submerged in 37° C. water.

C. Group C:
i. Used dip-spin process to apply EVAL primer layer, 1:1 DMSO:DMF (6000 rpm for one minute).
ii. Baked the stents at 140° C. for four hours in convection oven.
iii. Took weight measurements on each stent to the nearest microgram.
iv. Performed spray-coating process in CER under the following conditions: 3 passes, 3-second spray, no blow.
v. Weighed each sample at the end of the last pass to the nearest microgram.
vi. Baked the samples for 4 hrs at 60° C.
vii. Took weight measurements of each stent to the nearest microgram.
viii. Placed stents into the Tecoflex tubing with a balloon catheter—submerged in 37° C. water.

D. Group D:
i. Placed the samples flat on a sample holder. Perform argon plasma treatment.
ii. Spray coated primer layer (2% EVAL, 1:1 DMF:DMSO) onto the stents. Used 1.5 sec. spray time, 1–2 passes to achieve 10–40 micrograms of coating.
iii. Baked the stents at 140° C. for 4 hours in the convection oven.
iv. Took weight measurements on each stent to the nearest microgram.
v. Performed spray-coating process in CER at the following conditions: 3 passes, 3-second spray, no blow.
vi. Weighed each sample at the end of the last pass to the nearest microgram.
vii. Baked samples for 4 hrs at 60° C.
viii. Took weight measurements of each stent to the nearest microgram.
ix. Placed stents into the Tecoflex tubing with a balloon catheter—submerged in 37° C. water.

E. Group E:
i. Spray coated primer layer (2% EVAL, 1:1 DMF:DMSO) onto the stents. Used 1.5 sec. spray time, 1–2 passes to achieve 10–40 micrograms of coating.
ii. Baked the stents at 140° C. for four hours in convection oven.
iii. Took weight measurements on each stent to the nearest microgram.
iv. Performed spray-coating process in CER at the following conditions: 3 passes, 3-second spray, no blow.
v. Weighed each sample at the end of the last pass to the nearest microgram.
vi. Baked the samples for 4 hrs at 60° C.
vii. Took weight measurements of each stent to the nearest microgram.
viii. Placed the stents into the Tecoflex tubing with a balloon catheter—submerged in 37° C. water.

Test Procedure
1. Performed wet flow testing overnight for about 18 hrs.
2. Removed stents from the Tecoflex tubing with a stent catcher.
3. Counted the defects based on the number of peel defects at rings 1, 3, 5, and 7 on the stents' OD. Count the defects on the ID of the same rings.
4. Stent weight could not be a measurable because of the loss of the drug and uptake of water.
5. All test samples were handled with PPE appropriate for drug containing stents.

Data Summary and Results

| Group | Defects/Ring (OD) | Defects/Ring (ID) |
| --- | --- | --- |
| Control | 2.67 | 3.00 |
| Dip/Plasma | 0.67 | 0.47 |
| Dip/No Plasma | 0.87 | 0.80 |
| Spray/Plasma | 0.47 | 0.80 |
| Spray/No Plasma | 0.67 | 0.73 |

Discussion

Peel Defects of Primer Coated Stents vs. Untreated Controls

An improved adhesion, based on the number of peel defects, of the drug containing coating to the Tri-Star stent when an EVAL primer layer was applied is illustrated. All four treatment groups displayed significantly fewer peel defects per stent than the untreated control stents. Use of a spray-coated, 2% EVAL solution in 1:1 DMF:DMSO as a primer significantly improved adhesion of Actinomycin-D containing coating to the Tri-Star stents vs. the controls. The spray-coated primer produced slightly higher peel defect counts compared to the dip-spin deposited primer.

Example 34

Objective

The objective of this experiment was to test the adhesive properties of an Actinomycin-D containing coating to stainless steel stents having an EVAL primer layer. More specifically, this experiment attempted to illustrate the effect of different bake times on the final result. The coated stents were tested under wet flow conditions of saline heated to 37° C. The number of "peel defects" on a select number of stent rings was observed.

| Group | Treatment | Flow Rate |
| --- | --- | --- |
| A Control | None | 50 mL/min |
| B | Argon plasma treatment + EVAL primer layer by spray (2% EVAL, 1:1 DMF:DMSO) baked at 140° C. for 15 minutes | 50 mL/min |
| C | Argon plasma treatment + EVAL primer layer by spray (2% EVAL, 1:1 DMF:DMSO) baked at 140° C. for 30 minutes | 50 mL/min |
| D | Argon plasma treatment + EVAL primer layer by spray (2% EVAL, 1:1 DMF:DMSO) baked at 140° C. for 60 minutes | 50 mL/min |
| E | Argon plasma treatment + EVAL primer layer by spray (2% EVAL, 1:1 DMF:DMSO) baked at 140° C. for 120 minutes | 50 mL/min |

Materials and Equipment
1. 25, 13 mm Solo stents, cleaned ultrasonically in IPA for 15 minutes;
2. 25, balloon catheters or subassemblies to expand the stents;
3. 2% EVAL in 1:1 DMF:DMSO solution;
4. Actinomycin-D solution, 1:1 THF:DMSO with 3:1 EVAL:Act-D;
5. 3.0 mm Tecoflex tubing;
6. Saline;
7. Lint Free Wipes SU 00126 or equivalent;
8. 100% IPA;
9. Convection Oven;
10. Timer;
11. Plasma Machine;
12. Ultrasonic cleaner; and
13. Mettler balance with 0.1 micrograms resolution.

Preparation
1. Sonicated stents in IPA for 15 minutes.
2. Weighed each stent to the nearest microgram.
3. Prepared 5 stent samples for each group.

A. Group A (Control):
  i. Performed spray-coating process in CER under the following conditions: 3 passes, 3-second spray, no blow.
  ii. Weighed each sample at the end of the last pass to the nearest microgram.
  iii. Baked the samples for 240 minutes at 50° C.
  iv. Took weight measurements of each stent to the nearest microgram.
  v. Placed the stents into the Tecoflex tubing with a balloon catheter—submerged in 37° C. water.

B. Group B:
  i. Placed samples flat on sample holder. Perform argon plasma treatment.
  ii. Spray coated primer layer (2% EVAL, 1:1 DMF:DMSO) onto stents. Used 1.5 sec. spray time, 1–2 passes to achieve 10–40 micrograms of coating.
  iii. Baked the stents at 140° C. for 15 minutes in the convection oven.
  iv. Took weight measurements on each stent to the nearest microgram.
  v. Performed spray-coating process in CER under the following conditions: 3 passes, 3-second spray, no blow.
  vi. Weighed each sample at the end of the last pass to the nearest microgram.
  vii. Baked the samples for 240 minutes at 50° C.
  viii. Took weight measurements of each stent to the nearest microgram.
  ix. Placed stents into the Tecoflex tubing with a balloon catheter—submerged in 37° C. water.

C. Group C:
  i. Placed the samples flat on sample holder. Perform argon plasma treatment.
  ii. Spray coated primer layer (2% EVAL, 1:1 DMF:DMSO) onto stents. Used 1.5 sec. spray time, 1–2 passes to achieve 10–40 micrograms of coating.
  iii. Baked the stents at 140° C. for 30 minutes in the convection oven.
  iv. Took weight measurements on each stent to the nearest microgram.
  v. Performed spray-coating process in CER under the following conditions: 3 passes, 3-second spray, no blow.
  vi. Weighed each sample at the end of the last pass to the nearest microgram.
  vii. Baked the samples for 240 minutes at 50° C.
  viii. Took weight measurements of each stent to the nearest microgram.
  ix. Placed stents into the Tecoflex tubing with a balloon catheter—submerged in 37° C. water.

D. Group D:
  i. Placed samples flat on sample holder. Perform argon plasma treatment.
  ii. Spray coated primer layer (2% EVAL, 1:1 DMF:DMSO) onto stents. Used 1.5 sec. spray time, 1–2 passes to achieve 10–40 micrograms of coating.
  iii. Baked the stents at 140° C. for 60 minutes in the convection oven.
  iv. Took weight measurements on each stent to the nearest microgram.
  v. Performed spray-coating process in CER under the following conditions: 3 passes, 3-second spray, no blow.
  vi. Weighed each sample at the end of the last pass to the nearest microgram.
  vii. Baked the samples for 240 minutes at 50° C.
  viii. Took weight measurements of each stent to the nearest microgram.
  ix. Placed stents into the Tecoflex tubing with a balloon catheter—submerged in 37° C. water.

E. Group E:
  i. Placed samples flat on sample holder. Perform argon plasma treatment.
  ii. Spray coated primer layer (2% EVAL, 1:1 DMF:DMSO) onto stents. Used 1.5 sec. spray time, 1–2 passes to achieve 10–40 micrograms of coating.
  iii. Baked the stents at 140° C. for 120 minutes in the convection oven.
  iv. Took weight measurements on each stent to the nearest microgram.
  v. Performed spray-coating process in CER at the following conditions: 3 passes, 3-second spray, no blow.
  vi. Weighed each sample at the end of the last pass to the nearest microgram.
  vii. Baked samples for 240 minutes at 50° C.
  viii. Took weight measurements of each stent to the nearest microgram.
  ix. Placed stent into the Tecoflex tube with balloon catheter—submerged in 37° C. water.

Test Procedure
1. Performed wet flow testing overnight for about 18 hrs.
2. Removed the stents from the Tecoflex tubing with a stent catcher.
3. Counted the defects based on the number of peel defects at rings 3, 5, and 7 on the stents' OD. Count the defects on the ID of the same rings.
4. Stent weight could not be a measurable because of the loss of the drug and uptake of water.
5. All test samples were handled with PPE appropriate for drug containing stents.

Data Summary and Results

| Group | Total Defects per Stent |
| --- | --- |
| Control | 3.33 |
| 15 min bake | 1.00 |
| 30 min bake | 3.00 |
| 60 min bake | 1.67 |
| 120 min bake | 1.33 |

Discussion

The control group with no primer layer had significantly more peel defects as compared to the treatment groups with a primer layer. The groups with shorter baking times (15 and 30 minutes) had higher defect counts than the groups with longer baking times.

Example 35

Objective

The objective of this experiment was to test the adhesive properties of an Actinomycin-D containing coating on stainless steel stents having an EVAL primer layer. More specifically, different solvent systems (e.g., THF and DMF) were evaluated. The coated stents were tested under wet flow conditions of saline heated to 37° C. The number of "peel defects" on a select number of stent rings was observed.

| Group | Treatment | Flow Rate |
| --- | --- | --- |
| A Control | None | 50 mL/min |
| B | Argon plasma treatment + EVAL primer layer by spray (2% EVAL, 1:1 DMF:DMSO) baked at 140° C. for 15 minutes | 50 mL/min |
| C | Argon plasma treatment + EVAL primer layer by spray (2% EVAL, 1:1 DMF:DMSO) baked at 140° C. for 60 minutes | 50 mL/min |
| D | Argon plasma treatment + EVAL primer layer by spray (2% EVAL, 1:1 DMF:DMSO) baked at 140° C. for 240 minutes | 50 mL/min |
| E | Argon plasma treatment + EVAL primer layer by spray (2% EVAL, 1:1 THF:DMSO) baked at 140° C. for 60 minutes | 50 mL/min |

Materials and Equipment
1. 25, 13 mm Solo stents, cleaned ultrasonically in IPA for 15 minutes;
2. 25, balloon catheters or subassemblies to expand the stents;
3. 2% EVAL in 1:1 DMF:DMSO solution;
4. 2% EVAL in 1:1 THF:DMSO solution;
5. Actinomycin-D solution, 1:1 THF:DMSO with 3:1 EVAL:Act-D, 2% EVAL;
6. 3.0 mm Tecoflex tubing;
7. Saline;
8. Lint Free Wipes SU 00126 or equivalent;
9. 100% IPA;
10. Convection Oven;
11. Timer;
12. Plasma Machine;
13. Ultrasonic cleaner; and
14. Mettler balance with 0.1 micrograms resolution.

Preparation
1. Sonicated stents in IPA for 15 minutes.
2. Weighed each stent to the nearest microgram.
3. Prepared 5 stent samples for each group.
   A. Group A (Control):
      i. Performed spray-coating process in CER under the following conditions: 3 passes, 3-second spray, no blow.
      ii. Weighed each sample at the end of the last pass to the nearest microgram.
      iii. Baked samples for 240 minutes at 50° C.
      iv. Took weight measurements of each stent to the nearest microgram.
      v. Placed the stents into the Tecoflex tubing with a balloon catheter—submerged in 37° C. water.
   B. Group B:
      i. Placed samples flat on a sample holder. Performed argon plasma treatment.
      ii. Spray coated the primer layer (2% EVAL, 1:1 DMF:DMSO) onto the stents. Used 1.5 sec. spray time, 1–2 passes to achieve 10–40 micrograms of coating.
      iii. Baked the stents at 140° C. for 15 minutes in the convection oven.
      iv. Took weight measurements of each stent to the nearest microgram.
      v. Performed spray-coating process in CER under the following conditions: 3 passes, 3-second spray, no blow.
      vi. Weighed each sample at the end of the last pass to the nearest microgram.
      vii. Baked the samples for 240 minutes at 50° C.
      viii. Took weight measurements of each stent to the nearest microgram.
      ix. Placed the stents into the Tecoflex tubing with a balloon catheter—submerged in 37° C. water.
   C. Group C:
      i. Placed samples flat on a sample holder. Performed argon plasma treatment.
      ii. Spray coated the primer layer (2% EVAL, 1:1 DMF:DMSO) onto the stents. Used 1.5 sec. spray time, 1–2 passes to achieve 10–40 micrograms of coating.
      iii. Baked the stents at 140° C. for 60 minutes in the convection oven.
      iv. Took weight measurements of each stent to the nearest microgram.
      v. Performed spray-coating process in CER under the following conditions: 3 passes, 3-second spray, no blow.
      vi. Weighed each sample at the end of the last pass to the nearest microgram.
      vii. Baked the samples for 240 minutes at 50° C.
      viii. Took weight measurements of each stent to the nearest microgram.
      ix. Placed the stents into the Tecoflex tubing with a balloon catheter—submerged in 37° C. water.
   D. Group D:
      i. Placed samples on flat on a sample holder. Performed argon plasma treatment.

ii. Spray coated the primer layer (2% EVAL, 1:1 DMF:DMSO) onto the stents. Used 1.5 sec. spray time, 1–2 passes to achieve 10–40 micrograms of coating.
iii. Baked the stents at 140° C. for 240 minutes in the convection oven.
iv. Took weight measurements of each stent to the nearest microgram.
v. Performed spray-coating process in CER at the following conditions: 3 passes, 3-second spray, no blow.
vi. Weighed each sample at the end of the last pass to the nearest microgram.
vii. Baked the samples for 240 minutes at 50° C.
viii. Took weight measurements of each stent to the nearest microgram.
ix. Placed the stents into the Tecoflex tubing with a balloon catheter—submerged in 37° C. water.

E. Group E:
i. Placed samples flat on a sample holder. Perform argon plasma treatment.
ii. Spray coated the primer layer (2% EVAL, 1:1 THF:DMSO) onto the stents. Used 1.5 sec. spray time, 1–2 passes to achieve 10–40 micrograms of coating.
iii. Baked the stents at 140° C. for 60 minutes in the convection oven.
iv. Took weight measurements of each stent to the nearest microgram.
v. Performed spray-coating process in CER under the following conditions: 3 passes, 3 second spray, no blow.
vi. Weighed each sample at the end of the last pass to the nearest microgram.
vii. Baked the samples for 240 minutes at 50° C.
viii. Took weight measurements of each stent to the nearest microgram.
ix. Placed the stents into the Tecoflex tubing with a balloon catheter—submerged in 37° C. water.

Test Procedure
1. Performed wet flow testing overnight for about 18 hrs.
2. Removed the stents from the Tecoflex tubing with a stent catcher.
3. Counted the defects, based on the number of peel defects at rings 3, 5, and 7 on the stents' OD. Counted defects on the ID of the same rings.
4. The weight of the stents could not be a measurable because of the loss of the drug and uptake of water.
5. All test samples were handled with PPE appropriate for drug containing stents.

Data Summary and Results

| Group | Total Defects per Stent |
| --- | --- |
| No primer control | 0.00 |
| 15 min. bake | 0.00 |
| 60 min. bake | 0.33 |
| 240 min. bake | 0.00 |
| THF, 15 min. bake | 0.00 |

Example 36

Objective

The objective of this experiment was to test the adhesive properties of an Actinomycin-D containing coating on stainless steel stents having an EVAL primer layer made from a DMSO:THF solution applied to the stents. The coated stents were tested under wet flow conditions of saline heated to 37° C. The number of "peel defects" on a select number of stent rings was observed.

| Group | Treatment | Drying Time (min.) |
| --- | --- | --- |
| A | Argon plasma treatment + EVAL primer | 15 |
| B | Argon plasma treatment + EVAL primer | 30 |
| C | Argon plasma treatment + EVAL primer | 60 |
| D | Argon plasma treatment + EVAL primer | 90 |
| E | Argon plasma treatment + EVAL primer | 120 |

Materials and Equipment
1. 10, 13 mm SOLO stents, cleaned ultrasonically in IPA for 15 minutes;
2. 2% EVAL in 1:1 THF:DMSO solution;
3. 10 Balloon catheters or subassemblies to expand the stents;
4. Actinomycin-D solution, 1:1 THF:DMSO with 1:3 Act-D:EVAL, 2% EVAL;
5. 4.0 mm Tecoflex tubing;
6. Saline;
7. Lint Free Wipes SU 00126 or equivalent;
8. 100% IPA;
9. Convection Oven;
10. Timer;
11. Plasma Machine;
12. Ultrasonic cleaner;
13. Mettler balance with 0.1 microgram resolution;
14. Spray/bake mandrels and tips;
15. Flow Meter, N1429;
16. Microscope, minimum magnification 50×;
17. EFD controller with spray apparatus without translational stage; and
18. EFD controller with spray apparatus with translational stage.

Preparation
1. Sonicated the stents in IPA for 15 minutes.
2. Weighed each stent to the nearest microgram.
3. Prepare the stent samples for each group.
   A. Primer Coat
   i. Placed samples on sample holder. Performed argon plasma treatment.
   ii. Sprayed the primer layer (2% EVAL, 1:1 THF:DMSO) onto the stents with translational spray coater. Used 1.5 sec. for the spray time and speed 7 to achieve 10–40 μg of coating.
   iii. Baked the stents at 140° C. for the specified time in the convection oven.
   iv. Weighed the stents and recorded measurements to the nearest microgram.
   B. Drug Coat
   i. Sprayed the stents with a 3:1, EVAL:Act-D, 2% EVAL, 1:1 DMSO:THF solution for three seconds per pass for three passes. After each spray pass, dried the stents in the convection oven for 15 minutes at 50° C.
   ii. Weighed the stents and recorded measurements. If the drug coat weight matched the target weight, the stents were returned to the oven for 240 minutes. If weight gain did not match, the stents were returned to the glove box for additional spray coat application. Spray time on subsequent passes was adjusted to achieve target weight.

4. Wet Flow Test Sample Preparation
  A. Crimped the stents onto the balloon catheters.
  B. Inflated the stents to 4.0 mm in the Tecoflex tubing with the balloon catheters—submerged in 37° C. water
  C. Disposed Act-D contaminated water as hazardous waste.

Test Method/Procedure
1. Set flow rate at 50 ml/min.
2. Performed wet flow testing overnight for about 18 hrs.
3. Removed the stents from the Tecoflex tubing with a stent catcher.
4. Counted defects, based on the number of peel defects at rings 1, 3, 5, 7, and 10 on the stents' OD. Counted defects on the ID of the same rings.
5. All test samples were handled with PPE appropriate for drug containing stents.

Data Summary and Results

| Drying Time (min.) | Total Defects per Stent | Total Defects per Stent (end rings) | Total Defects per Stent (middle rings) |
|---|---|---|---|
| 15 | 0.0 | 0.0 | 0.0 |
| 30 | 2.0 | 2.0 | 0.0 |
| 60 | 1.0 | 1.0 | 0.0 |
| 90 | 0.0 | 0.0 | 0.0 |
| 120 | 0.5 | 0.5 | 0.0 |

Example 37

Multi-Link Tetra™ stents (available from Guidant Corporation) were provided. A 2% EVAL solution in dimethyl acetamide (DMAC) was prepared. The stents were sprayed with the 2% EVAL solution. The stents were then heated in an for about 1 hour at about 140° C. to essentially remove the DMAC solvent from the layer to form a primer coating. The weight of EVAL on the primer coating was determined to be about 160 µg. Another solution was prepared containing a mixture of EVAL and the active ingredient Clobetasol in a DMAC solvent. The EVAL-Clobetasol solution was then sprayed onto the primer coating. The stents were then heated in an oven for about 2 hours at about 50° C. to essentially remove the DMAC solvent to form a drug reservoir region. The weight of the reservoir region was determined to be about 500 µg. Next, the stents were sprayed with the 2% EVAL solution. The stents were then heated in an oven for about 2 hours at about 50° C. to essentially remove the DMAC solvent to form a barrier region. The weight of the barrier region was determined to be about 300 µg.

After final drying, the coatings were transparent giving the stents a glossy-like shine. The stents were exposed to simulation tests by being expanded to about 3 mm. No peeling was detected. Also, it was calculated that as applied, the coating in total contained 2% EVAL, 2% Clobetasol and 96% DMAC by weight.

Example 38

18 mm Vision-D stents (cobalt-chromium alloy stents prepared for Guidant Corporation) were provided. The stents were separated into different test groups to investigate two variables: (1) the thickness of the primer layer and (2) the drug:polymer ratio.

A primer solution was prepared by mixing poly(butyl methacrylate) (PBMA) with a solvent containing 60% acetone and 40% xylene to produce a 2% PBMA solution. Stents from selected test groups were sprayed with the 2% PBMA solution with multiple spray cycles. After each spray repetition, warm air was directed onto the stents to facilitate evaporation. The stents were then heated in an oven for about ½ hour at about 80° C. to essentially remove the solvent from the layer to form a primer coating. Then, the weight of PBMA on the primer coatings was determined.

The following table summarizes the spray process parameters for each of the layers, including the primer layer:

| Parameter | Set Value | Units |
|---|---|---|
| Spray Nozzle | | |
| Spray nozzle temperature | Room Temperature | ° C. |
| Atomization pressure (non-activated) | 15 ± 2.5 | psi |
| Distance from spray nozzle to coating mandrel pin | 10–12 | mm |
| Solution barrel pressure | about 2.5 | psi |
| Needle valve lift pressure | 80 ± 10 | psi |
| Air Nozzle | | |
| Temperature | Room Temperature | ° C. |
| Air Pressure | 12–15 | psi |
| Distance from heat nozzle to coating mandrel pin | 10–15 | mm |

Another solution was prepared by mixing PBMA and the active ingredient 40-O-(2-hydroxy)ethyl-rapamycin (EVEROLIMUS) in a solvent containing 60% acetone and 40% xylene. The polymer-drug solution was then sprayed onto the primer coating with the same spray process parameters as for the application of the primer coating. The amount of drug solution sprayed onto the individual stents depended on the test group. Each test group contained 3 stents. The stents were then heated in an oven for ½ hour at 80° C. to essentially remove the solvent to form a drug reservoir layer. The weight of the reservoir region was then determined.

A barrier layer solution was prepared by mixing PBMA with a solvent containing 15% acetone, 40% xylene and 45% hydrofluoroether (HFE) (Novec™ Engineered Fluid HFE-7100, available from 3M Specialty Materials, St. Paul, Minn.) to produce a 2% PBMA solution. The PBMA solution was then sprayed onto the reservoir coating with the same spray process parameters as for the application of the primer coating. The stents were then heated in an oven for about ½ hour at about 80° C. to essentially remove the solvent to form a barrier layer.

After final drying, the coatings were expanded to test the mechanical integrity of the coating. In particular, the stents from each test group were expanded to an inner diameter of about 3.5 mm at about 37° C. in water. The coatings were then studied using a Scanning Electron Microscope (SEM) to determine if there were visible cracks as a result of the expansion of the stents. As the results demonstrate in the following table, the stents with a thicker primer layer have greater mechanical integrity:

| Drug to Polymer Ratio | Primer Layer (µg) | Reservoir Layer (µg) | Total Drug Content (µg) | Cracks Visible in Coating? |
|---|---|---|---|---|
| 1:1.25 | 0 | 360 | 160 | Yes |
|  | 60 | 360 | 160 | Yes |
|  | 120 | 360 | 160 | No |
| 1:1.35 | 0 | 376 | 160 | Yes |
|  | 60 | 376 | 160 | Yes |
|  | 120 | 376 | 160 | No |
| 1:1.50 | 0 | 400 | 160 | Yes |
|  | 60 | 400 | 160 | No |
|  | 120 | 400 | 160 | No |

Example 39

18 mm Vision-D stents were provided. The stents were separated into different test groups to investigate three variables: (1) the thickness of the primer layer, (2) the drug:polymer ratio and (3) the type of polymer used for primer layer.

A first primer solution was prepared by mixing PBMA with a solvent containing 60% acetone and 40% xylene to produce a 2% PBMA solution. A second primer solution was prepared by mixing EVAL with a solvent containing 80% dimethyl acetamide (DMAC) and 20% pentane to produce a 4% EVAL solution. Stents from selected test groups were sprayed with either the 2% PBMA solution or the 4% EVAL solution with multiple spray cycles. After each spray repetition, warm air was directed onto the stents to facilitate evaporation. The stents were then heated in an oven for about 2 hours at about 80° C. to essentially remove the solvent from the layer to form a primer coating. Then, the weight of PBMA or EVAL on the primer coatings was determined.

The following table summarizes the spray process parameters for each layer, including the primer layer:

| Parameter | Set Value | Units |
| --- | --- | --- |
| Spray Nozzle | | |
| Spray nozzle temperature | 65 ± 1 (primer and barrier layers); 45 ± 1 (reservoir layer) | ° C. |
| Atomization pressure (non-activated) | 20 ± 1 | psi |
| Distance from spray nozzle to coating mandrel pin | 10–12 | mm |
| Solution barrel pressure | 2.25 ± 1.25 | psi |
| Needle valve lift pressure | 66 ± 5 | psi |
| Flow Rate for Primer Layer | 15 ± 3 | μg/cycle |
| Flow Rate for Drug Layer | 30 ± 4 | μg/cycle |
| Flow Rate for Barrier Layer | 15 ± 3 | μg/cycle |
| Air Nozzle | | |
| Temperature (approximate temperature at stent surface with 110° C. setting for nozzle) | 80 ± 5 | ° C. |
| Air Pressure | 12–15 | psi |
| Distance from heat nozzle to coating mandrel pin | 10–15 | mm |
| Oven Drying Conditions | | |
| Oven temperature | about 80 | ° C. |
| Drying Time | about 2.0 | Hours |

Another solution was prepared by mixing EVAL and the active ingredient Everolimus in a solvent containing 80% DMAC and 20% pentane. The polymer-drug solution was then sprayed onto the primer coating. The amount of drug solution sprayed onto the individual stents depended on the test group. Each test group contained 5 stents. The stents were then heated in an oven for 2 hours at 80° C. to essentially remove the solvent to form a drug reservoir layer. The weight of the reservoir region was then determined.

A barrier layer solution was prepared by mixing EVAL with a solvent containing 80% DMAC and 20% pentane to produce a 4% EVAL solution. The EVAL solution was then sprayed onto the reservoir coating. The stents were then heated in an oven for 2 hours at 80° C. to essentially remove the solvent to form a barrier layer. The following table summarizes the parameters for the test groups:

| Group | Primer Layer (μg) | Total Drug Content (μg) | Drug to Polymer Ratio | Reservoir Layer (μg) | Barrier Layer (μg) | Total Coating Weight (μg) |
| --- | --- | --- | --- | --- | --- | --- |
| A1 | 120 (EVAL) | 160 | 1:1.25 | 360 | 100 | 580 |
| A2 | 160 (EVAL) | 160 | 1:1.25 | 360 | 100 | 620 |
| B1 | 120 (EVAL) | 160 | 1:2.3 | 528 | 100 | 748 |
| B2 | 160 (EVAL) | 160 | 1:2.3 | 528 | 100 | 788 |
| C1 | 65 (EVAL) | 160 | 1:1.25 | 360 | 100 | 525 |
| D1 | 120 (PBMA) | 160 | 1:1.25 | 360 | 100 | 580 |
| D2 | 160 (PBMA) | 160 | 1:1.25 | 360 | 100 | 620 |
| E1 | 120 (PBMA) | 160 | 1:2.3 | 528 | 100 | 748 |
| E2 | 160 (PBMA) | 160 | 1.2.3 | 528 | 100 | 788 |
| F1 | 65 (PBMA) | 160 | 1:1.125 | 360 | 100 | 525 |

After final drying, the coatings were expanded to test the mechanical integrity of the coating. In particular, the stents from each test group were hydrated in about 37° C. water for about 5 minutes. The stents were then expanded to have an inner diameter of about 3.5 mm with the use of a balloon catheter. The stents were then dried at about 37° C. and studied using a SEM to determine if there were visible cracks as a result of the expansion of the stents.

Figure 8A:
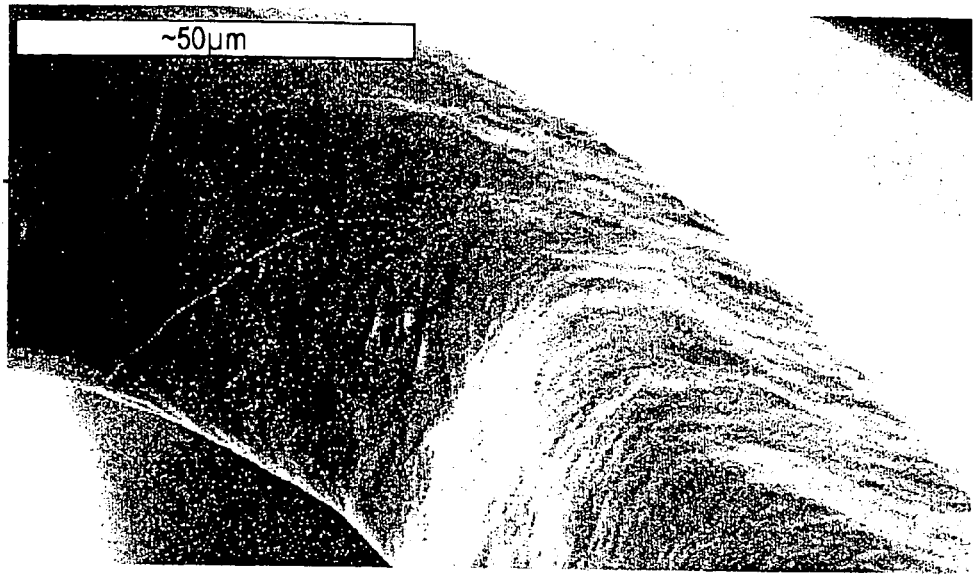
FIG. 8A is a Scanning Electron Microscope photograph of a stent coating having a primer layer with ethylene vinyl alcohol copolymer applied in accordance with Example 39.
Figure 8B:
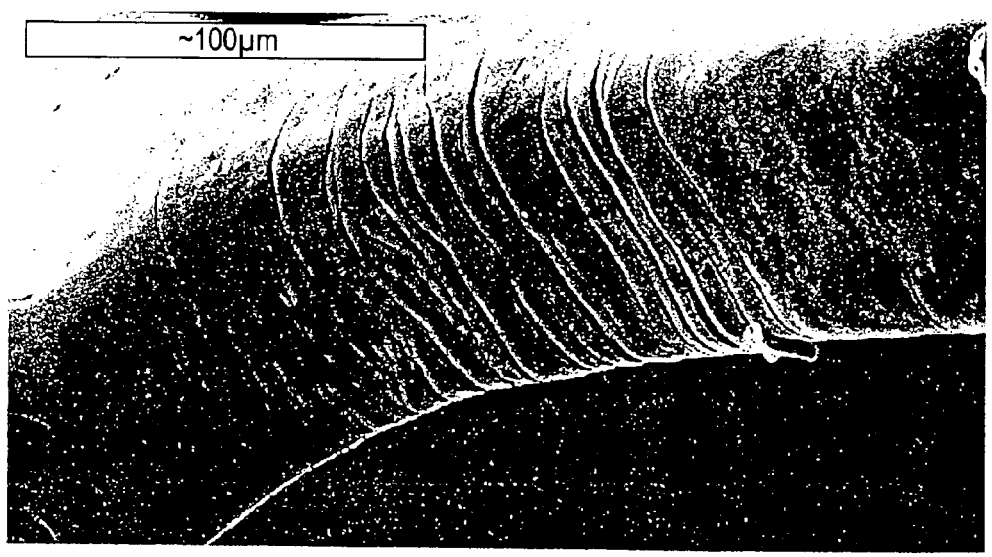
FIG. 8B is a Scanning Electron Microscope photograph of a stent coating having a primer layer with ethylene vinyl alcohol copolymer applied in accordance with Example 39.

The SEM photos of the stents with an EVAL primer layer showed that the number and severity of cracks were reduced with an increase in the thickness of the primer coating. The results also suggest that as the drug to polymer ratio increases, the thickness of the primer layer should be increased in order to prevent or reduce cracking. The least number of cracks was observed in the group B2 (FIG. 8A) which had significantly fewer cracks than group C1 which had a relatively thin primer layer (FIG. 8B). Group B2 had 160 μg of EVAL primer and the drug to polymer ratio was 1:2.3 (i.e., about 30% drug loading).

Figure 9A:
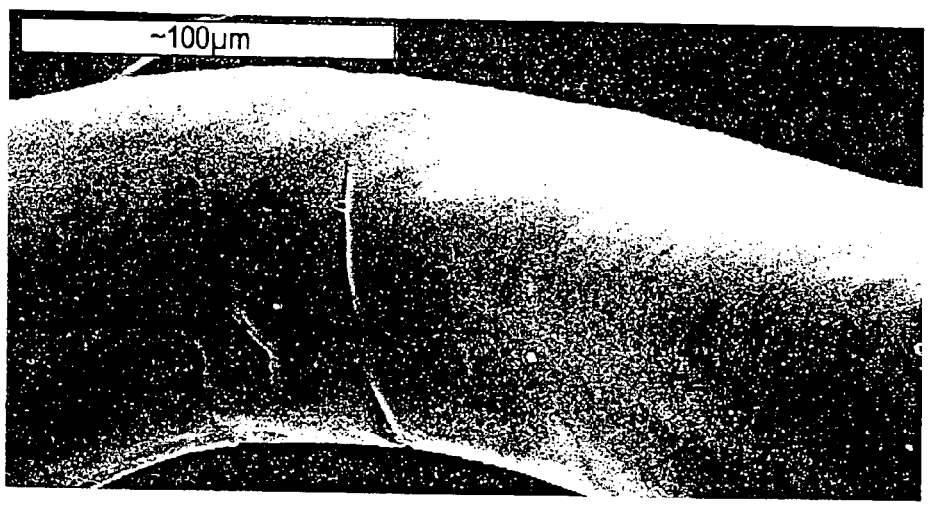
FIG. 9A is a Scanning Electron Microscope photograph of a stent coating having a primer layer with poly(butyl methacrylate) applied in accordance with Example 39.
Figure 9B:
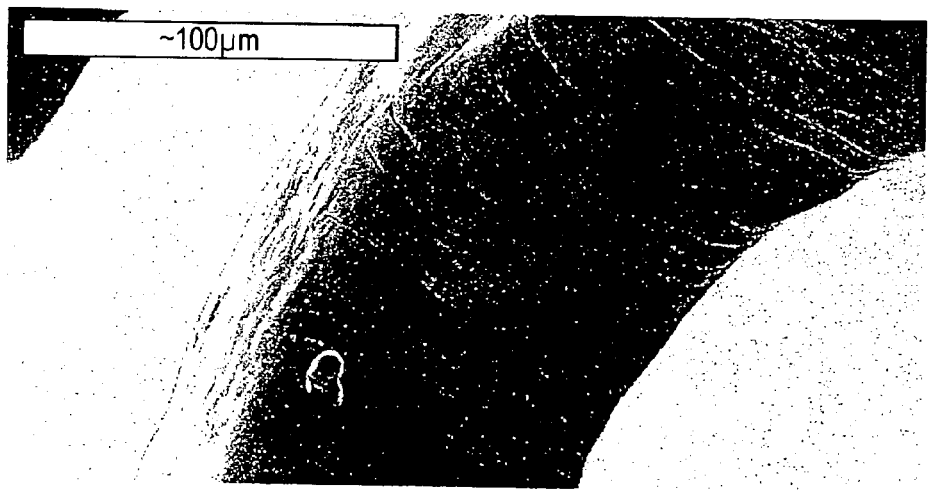
FIG. 9B is a Scanning Electron Microscope photograph of a stent coating having a primer layer with poly(butyl methacrylate) applied in accordance with Example 39.

The SEM photos of the stents with a PBMA primer layer also showed that the number and severity of cracks were reduced with an increase in the thickness of the primer coating. For example, the group E2 with 160 μg of primer (FIG. 9A) had significantly fewer cracks than Group F1 (FIG. 9B).

Example 40

This Example describes the formation of a porous matrix for a primer layer. A 4% (w/w) PBMA solution is prepared by gently mixing the PBMA with a solvent solution containing 60% acetone, 20% xylene and 20% ethylene glycol. The ethylene glycol is a less compatible solvent for PBMA than acetone and xylene. The polymer solution is applied to an 18 mm Vision-D stent. The stent is then heated in an oven for ½ hour at 80° C. to essentially remove the solvent to form a primer layer A porous matrix forms in the primer layer during the evaporation step because of the presence of the ethylene glycol in the composition.

Example 41

This Example describes the formation of a porous matrix for a primer layer. EVAL pellets are provided. An EVAL powder is formed by cryogenically grinding the pellets. After grinding, the powder has an average particle size of about 1 micron to about 10 microns. The powder is applied to the outer surface of an 18 mm Vision-D stent. The adhesion of the powder to the stent surface can be improved by first mixing the polymeric powder with a small portion of a non-solvent to give the powder a paste-like consistency. Pressure is then applied to the powder on the stent so that the particles are pressed together. Then, the stent is placed in an oven and heated at about 150° C. to about 170° C. for about 15 minutes to about 1 hour. After this sintering process, space remains between the lattice of the EVAL particles to form porous cavities.

Example 42

This Example describes the formation of a porous matrix for a primer layer. A 2% (w/w) EVAL solution in 80% DMAC and 20% pentane is prepared. The polymer solution is applied to an 18 mm Vision-D stent. A solution of 100% pentane is then applied to the stent surface to precipitate the polymer to form a porous matrix. The stent is then heated in an oven for 2 hours at 80° C. to essentially remove the solvent to form a primer layer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of forming a coating for an implantable device, comprising:

forming a primer layer comprising a polymer on at least a portion of a surface of an implantable device, wherein the primer layer has a weight measurement of X;

forming a reservoir layer comprising a polymer and an active ingredient on at least a selected portion of the primer layer, wherein the reservoir layer has a weight measurement of Y; and wherein X/Y is equal to or greater than 0.25 and equal to or less than 20.

2. The method of claim 1, wherein the coating has a drug loading equal to or greater than 30% by weight based on the total weight of the reservoir layer.

3. The method of claim 1, wherein X/Y is equal to or greater than 0.33.

4. The method of claim 1, further comprising forming a barrier layer on at least a selected portion of the reservoir layer to reduce the rate at which the active ingredient is released from the reservoir layer after insertion of the device into a body of a patient.

5. The method of claim 1, wherein the primer layer comprises an ethylene vinyl alcohol copolymer or poly(butyl methacrylate).

6. The method of claim 1, further comprising forming asperities on the surface of the primer layer preceding the formation of the reservoir layer.

7. The method of claim 1, wherein the primer layer includes at least a region having a degree of porosity.

8. A method of forming a coating for an implantable device, comprising:

forming a primer layer comprising a polymer on at least a portion of a surface of an implantable device, wherein the primer layer has a thickness X;

forming a reservoir layer comprising a polymer and an active ingredient on at least a selected portion of the primer layer, wherein the reservoir layer has a thickness Y; and wherein X/Y is equal to or greater than 0.25 and equal to or less than 20.

9. The method of claim 8, wherein the thickness X is about 0.5 microns to about 3 microns and the thickness Y is about 1 micron to about 10 microns.

10. An implantable device comprising a coating for delivery of an active ingredient, wherein the coating includes:

a primer region comprising a polymer on at least a portion of a surface of an implantable device, wherein the primer region has a thickness X;

a reservoir region comprising a polymer and an active ingredient on at least a selected portion of the primer region, wherein the reservoir region has a thickness Y; and wherein the thickness X is measured from the outer surface of the primer region to the surface of the implantable device prior to the migration of the active ingredient from the reservoir region to the primer region, and wherein X/Y is equal to or greater than 0.25 and equal to or less than 20.

11. The implantable device of claim 10, wherein the implantable device is selected from a group of balloon-expandable stents and self-expandable stents.

12. The implantable device of claim 10, wherein the primer region or the reservoir region comprises an ethylene vinyl alcohol copolymer or poly(butyl methacrylate).

13. The implantable device of claim 10, wherein the active ingredient is selected from a group of heparin, heparin sulfate, heparin having a hydrophobic counterion, mannose-6-phosphate, superoxide dismutase, clobetasol, retinoic acid, rapamycin, rapamycin analogs and derivatives, suramin, asiaticoside, hyaluronan and combinations thereof.

14. The implantable device of claim 10, further including a barrier region located on at least a selected portion of the reservoir region for reducing the rate at which the active ingredient is released from the coating after insertion of the device into a body of a patient.

15. The implantable device of claim 10, wherein the primer region includes a porous matrix extending from the interface of the primer region and the reservoir region into the primer.

16. A stent comprising a coating for delivery of an active ingredient, wherein the coating includes a primer region comprising a polymer and a reservoir region comprising a polymer and an active ingredient, and wherein the thickness or the weight of the primer region is sufficiently high so as to allow drug loading of 30% in the reservoir region without causing the coating to significantly crack when the stent is expanded.

17. The method of claim 8 wherein the coating has a drug loading equal to or greater than 30% by weight based on the total weight of the reservoir layer.

18. The method of claim 8 wherein X/Y is equal to or greater than 0.33.

19. The method of claim 8 further comprising forming a barrier layer on at least a selected portion of the reservoir layer to reduce the rate at which the active ingredient is released from the reservoir layer after insertion of the device into a body of a patient.

20. The method of claim 8 wherein the device is a stent.

21. The method of claim 8 wherein the active ingredient comprises rapamycin or analogs and derivatives thereof.

22. The method of claim 8 wherein the primer region or the reservoir region comprises poly(butyl methacrylate) or an ethylene vinyl alcohol compolymer.

23. The implantable device of claim 10 wherein the coating has a drug loading equal to or greater than 30% by weight based on the total weight of the reservoir layer.

24. The implantable device of claim 10 wherein X/Y is equal to or greater than 0.33.

25. The implantable device of claim 10 wherein the active ingredient comprises rapamycin or analogs and derivatives thereof.

26. The stent of claim 16 wherein the primer region or the reservoir region comprises an ethylene vinyl alcohol copolymer or poly(butyl methacrylate).

27. The stent of claim 16 wherein the active ingredient comprises rapamycin or analogs and derivatives thereof.

28. The stent of claim 16 further including a barrier region located on at least a selected portion of the reservoir region for reducing the rate at which the active ingredient is released from the coating after insertion of the device into a body of a patient.

29. The stent of claim 16 wherein the primer region includes at least a region having a degree of porosity.

30. The method of claim 1 wherein the reservoir layer comprises an ethylene vinyl alcohol copolymer or poly (butyl methacrylate).

31. The method of claim 1 wherein the active ingredient comprises rapamycin or analogs and derivatives thereof.

32. The method of claim wherein the device is a stent.

* * * * *